US010383825B2

(12) United States Patent
Lebo et al.

(10) Patent No.: US 10,383,825 B2
(45) Date of Patent: Aug. 20, 2019

(54) CALCIUM ALGINATE DOSAGE FORMULATIONS, AND METHODS OF MAKING AND USING THEREOF

(71) Applicant: Temple University-Of The Commonwealth System of Higher Education, Philadelphia, PA (US)

(72) Inventors: David B. Lebo, Warminster, PA (US); Suzan Owaisat, Philadelphia, PA (US)

(73) Assignee: TEMPLE UNIVERSITY—OF THE COMMONWEALTH SYSTEM OF HIGHER EDUCATION, Philadelphia, PA (US)

( * ) Notice: Subject to any disclaimer, the term of this patent is extended or adjusted under 35 U.S.C. 154(b) by 0 days.

(21) Appl. No.: 15/235,360

(22) Filed: Aug. 12, 2016

(65) Prior Publication Data
US 2017/0042820 A1    Feb. 16, 2017

Related U.S. Application Data

(60) Provisional application No. 62/204,715, filed on Aug. 13, 2015.

(51) Int. Cl.
| A61K 9/20 | (2006.01) |
| A61K 9/28 | (2006.01) |
| A61K 9/00 | (2006.01) |
| A61K 31/192 | (2006.01) |
| A61K 31/09 | (2006.01) |
| A61K 31/522 | (2006.01) |
| A61K 31/734 | (2006.01) |
| A61N 1/32 | (2006.01) |

(52) U.S. Cl.
CPC ............ *A61K 9/205* (2013.01); *A61K 9/0009* (2013.01); *A61K 9/2013* (2013.01); *A61K 9/2054* (2013.01); *A61K 9/2095* (2013.01); *A61K 9/282* (2013.01); *A61K 9/286* (2013.01); *A61K 9/2866* (2013.01); *A61K 31/09* (2013.01); *A61K 31/192* (2013.01); *A61K 31/522* (2013.01); *A61K 31/734* (2013.01); *A61N 1/325* (2013.01)

(58) Field of Classification Search
None
See application file for complete search history.

(56) References Cited

U.S. PATENT DOCUMENTS

| 3,640,741 A | 2/1972 | Etes | |
| 4,778,888 A * | 10/1988 | Fulton | C08B 37/0039 544/208 |
| 5,204,111 A | 4/1993 | Handjani et al. | |
| 5,705,190 A * | 1/1998 | Broad | A61K 9/2013 424/465 |
| 5,840,777 A * | 11/1998 | Eagles | A61L 15/28 521/134 |
| 5,985,323 A * | 11/1999 | Augello | A61K 9/1652 424/464 |
| 2002/0001619 A1 | 1/2002 | Goldenberg et al. | |
| 2003/0235628 A1 * | 12/2003 | Taneja | A61K 9/0095 424/687 |
| 2005/0220878 A1 * | 10/2005 | Fegely | A61K 9/282 424/473 |
| 2005/0260263 A1 | 11/2005 | Hsiao et al. | |
| 2006/0280795 A1 * | 12/2006 | Penhasi | A61K 9/4891 424/472 |
| 2007/0191757 A1 | 2/2007 | Steiner et al. | |
| 2008/0103206 A1 | 5/2008 | Swann et al. | |
| 2008/0233197 A1 * | 9/2008 | Matthews | A61K 9/4808 424/490 |
| 2009/0123537 A1 * | 5/2009 | DeBrouse | A61K 9/1611 424/463 |
| 2012/0276017 A1 | 3/2012 | Lickrish et al. | |
| 2013/0005816 A1 | 1/2013 | Chen et al. | |
| 2013/0028970 A1 | 1/2013 | Schwier et al. | |

FOREIGN PATENT DOCUMENTS

| CN | 1810867 | 2/2006 |
| EP | 0188040 B1 | 1/1985 |
| WO | 2014190440 | 5/2014 |

OTHER PUBLICATIONS

Khazaeli et al., Iranian Journal of Pharmaceutical Research, 2008, 7(3), 163-170.*
Mandal et al., Brazilian Journal of Pharmaceutical Sciences, 2010, 46(4), 785-793.*
Haida et al., J. Med. Dent. Sci., 2012, 69, 9-16.*
Shun Yih Lin for the degree of Doctor of Philosophy in Pharmacy presented on Aug. 2, 1990. Title: Calcium Alginate Gels In Oral Dosage Form Design, pp. 1-250.*
U.S. Appl. No. 09/529,603, filed Sep. 17, 2002, Kawashima et al.
Wong, Tin Wui, "Alginate graft copolymers and alginate-coexcipient physical mixture in oral drug delivery", Journal of Pharmacy and Pharmacology 2011. 63:1497-1512.
Gharravi et al., "Design and Fabrication of Anatomical Bioreactor Systems Containing Alginate Scaffolds for Cartilage Tissue Engineering", Avicenna Journal of Medical Biotechnology, 2012. 4(2):65-75.
Lersch, Martin. "First experiments with sodium alginate", Khymos, WordPress, 2007. <http://blog.khymos.org/2007/03/30/first-experiments-with-sodium-alginate/>; pp. 1-17.
Ying, Xiaoguang et al., "Stimuli-responsive recognition of BSA-imprinted poly vinyl acetate grafted calcium alginate core-shell hydrogel microspheres", J. Appl. Polym. Sci., 2013. 127(5):3898-3909.
Yuk et al., "Electric Current-Sensitive Drug Delivery Systems Using Sodium Alginate/Polyacrylic Acid Composites", 1992, Pharmaceutical Research, 9(7):955-957.
Smrdel et al., "Characterization of Calcium Alginate Beads Containing Structurally Similar Drugs", Drug Development and Industrial Pharmacy, 2006. 32:623-633.

(Continued)

*Primary Examiner* — Abigail Vanhorn
(74) *Attorney, Agent, or Firm* — Riverside Law LLP

(57) ABSTRACT

An alginate and stearic acid composition is described, including methods of molding it into tablets further comprising a drug, and methods of controlling the drug release from the tablets.

23 Claims, 36 Drawing Sheets

(56) References Cited

OTHER PUBLICATIONS

Almeida and Almeida, "Cross-linked alginate-gelatine beads: a new matrix for controlled release of pindolol", Journal of Controlled Release, 2004. 97: 431-439.
Pasparakis and Bouropoulos, "Swelling studies and in vitro release of verapamil from calcium alginate and calcium alginate-chitosan beads", International Journal of Pharmaceutics, 2006. 323:34-42.
Tonnesen and Karlsen, "Alginate in Drug Delivery Systems", Drug Development and Industrial Pharmacy, 2002. 28(6); 621-630.
Kakita et al., "Some properties of alginate gels derived from algal sodium alginate", J Appl Phycol, 2008. 20:543-549.
Bajpai and Sharma, "Sharma S Investigation of swelling/degradation behaviour of alginate beads crosslinked with $Ca^{2+}$ and $Ba^{2+}$ ions", Reactive & Functional Polymers, 2004. 59:129-140.
Kim and Lee, "The controlled release of blue dextran from alginate beads", International Journal of Pharmaceutics, 1992. 79:11-19.
Wang et al., "Alginate/starch blend fibers and their properties for drug controlled release", Carbohydrate Polymers, 2010. 82: 842-847.
Kunal and Mehta, "A Review on Oral Osmotically Driven Systems", International Journal of Pharmacy and Pharmaceutical Sciences, 2013. 5:1005-1013.
Waterman et al., "Osmotic capsules: A universal oral, controlled-release drug delivery dosage form", Journal of Controlled Release, 2011. 152: 264-269.
Mani et al., "Solubility of Guaifenesin in the Presence of Common Pharmaceutical Additives", Pharmaceutical Development and Technology, 2003. (4):385-396.
Pillay and Fassihi, "In vitro release modulation from crosslinked pellets for site-specific drug delivery to the gastrointestinal tract I. Comparison of pH-responsive drug release and associated kinetics", Journal of Controlled Release, 1999. 59:229-242.
Sinha and Kumira, "Polysaccharide Matrices for Microbially Triggered Drug Delivery to the Colon", European Journal of Pharmaceutical Sciences, 2003. 18:3-18.

* cited by examiner

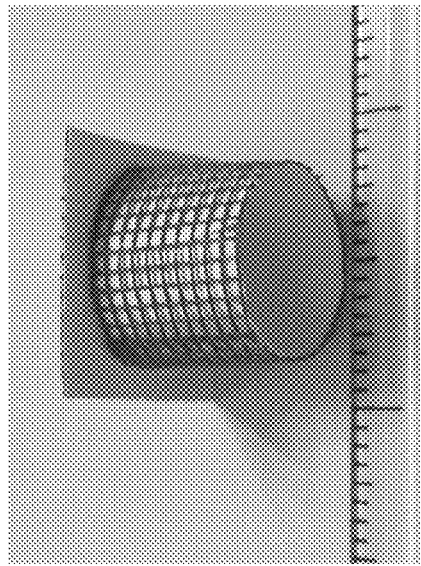
Figure 3B
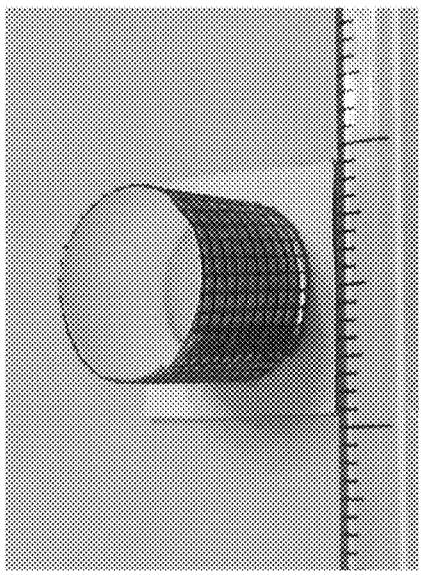
Figure 3A
Figure 3

CALCIUM ALGINATE DOSAGE FORMULATIONS, AND METHODS OF MAKING AND USING THEREOF

CROSS-REFERENCE TO RELATED APPLICATIONS

This application claims priority from U.S. Provisional Patent Application Ser. No. 62/204,715, filed Aug. 13, 2015, the entire contents of which is incorporated herein by reference.

FIELD OF THE INVENTION

Embodiments of the invention relate to calcium alginate formulations for administration of bioactive agents, methods of producing the formulations incorporating bioactive agents, methods of releasing bioactive agents from the formulations, and methods for treatment of diseases or disorders.

BACKGROUND

Alginic acid is a soluble polysaccharide extracted mainly from brown algae such as Laminariales and Fucales species (Kakita et al., 2008, J Appl Phycol, 20:543-549). The alginate chain is made of the following regions: two homopolymeric regions of β-d-mannuronic acid (M) blocks and α-1-guluronic acid (G) blocks, interdispersed with regions of alternating structure of α-1-guluronic and β-d-mannuronic acid blocks (Wui, 2011, Journal of Pharmacy and Pharmacology, 63: 1497-1512). An insoluble gel composed of three-dimensional network is formed upon gelation process of alginate when blocks of guluronic acid residues interact ionically with divalent cations such as $Ca^{+2}$. This network is usually described by the egg box model (Bajpai and Sharma, 2004, Reactive & Functional Polymers, 59:129-140).

Alginate is reported to be generally non-toxic, biodegradable, non-immunogenic and biocompatible. Thus, these advantages suggest that alginic beads may be suitable for oral administration (Wui, 2011, Journal of Pharmacy and Pharmacology, 63: 1497-1512). Sodium alginate is the salt of alginic acid. When small drops of sodium alginate solution are dropped into calcium chloride solution a cation exchange between $Na^+$ and $Ca^{2+}$ takes place and a spherical gel with regular shape and size is obtained. The spherical gel is termed 'alginate bead' (Kim and Lee, 1992, International Journal of Pharmaceutics, 79:11-19).

Alginate beads are insoluble and significantly reduce its swelling in the presence of the solvent as the degree of cross-linking increases. This generally results in a reduction of the permeability of different solutes. As a consequence, the release of embodied drugs in alginate matrices will be delayed, allowing these systems to be used in drug controlled release (Wang et al., 2010, Carbohydrate Polymers, 82: 842-847). However, degradation events can take place through loss of calcium alginate cross linkages through reaction of $Ca^{2+}$ with $PO_4^{3-}$ which are removed by precipitation as $Ca_3(PO_4)_2$ (Wui, 2011, Journal of Pharmacy and Pharmacology, 63: 1497-1512).

Alginates are among the most widely used biopolymers in the field of pharmaceutics. They are conventionally used as an excipient in drug products due to their thickening, gel-forming, and stabilizing properties (Tønnesen and Karlsen, 2002, Drug Development and Industrial Pharmacy, 28(6); 621-630). Alginate salt solution has the ability to form an insoluble gel in the presence of multivalent ions such as $Ca^{++}$ and $Zn^{++}$, which can be utilized to prepare multiparticulate systems-beads-incorporating numerous drugs, proteins, cells, or enzymes that can be released in a controlled manner (Smrdel et al., 2006, Drug Development and Industrial Pharmacy, 32:623-633). Ionotropic gelation is the commonly used method to produce alginate beads, where the dispersion of alginate and material to be incorporated is added drop wise into a multivalent ion solution (Smrdel et al., 2006, Drug Development and Industrial Pharmacy, 32:623-633). Therefore, alginate can play a significant role in the design of a tailored controlled-release product. However, limitations such as some difficulties in the preparation process, in addition to quality control challenges due to the small size of these beads limit the feasibility of producing them in large scale to be introduced into the market.

Alginate has been formulated into different dosage forms to deliver drugs orally. One of these dosage forms is calcium alginate beads (Wui, 2011, Journal of Pharmacy and Pharmacology, 63: 1497-1512). Generally, different methods can be used to manufacture beads such as: dripping emulsification and coacervation, rotating-disc atomization, air jet, atomization, electrostatic dripping, mechanical cutting, and the vibrating nozzle technique (Nussinovitch, 2010, Polymer Macro- and Micro-Gel Beads: Fundamentals and applications, Springer, 2010:2). However, some of these techniques suffer from different limitations. One of these limitations is the difficulty in achieving the simultaneous production of beads at a high production rate with a satisfactory level of material utilization under mild and non-toxic conditions or under completely sterile conditions. Another difficulty is the ability to scale-up the process that will produce beads with a narrow size distribution. (Nussinovitch, 2010, Polymer Macro- and Micro-Gel Beads: Fundamentals and applications, Springer, 2010:2). Also, there is a maximum concentration of polymer for producing spherical beads. This means that there is a limit to the capability to retarding the drug release. This limits its use as a controlled release polymer. Most importantly, the small size of the beads presents a major limitation due to high drug loss during bead preparation (Almeida and Almeida, 2004, Journal of Controlled Release, 97: 431-439).

Natural polymers have attracted a lot of attention in oral drug delivery due to their safety, biodegradability, and biocompatibility (Almeida and Almeida, 2004, Journal of Controlled Release, 97: 431-439). Sodium alginate is one of the biopolymers that has been formulated as microspheres, microcapsules, gel beads, hydrogel, film, nanoparticles and tablets due to the inert environment within its network which allows for the entrapment of a wide range of bioactive substances, cells and drug molecules (Pasparakis and Bouropoulos, 2006, International Journal of Pharmaceutics, 323: 34-42). One of the unique properties of sodium alginate is its ability to form an insoluble gel when it comes in contact with divalent cations. Beads; called calcium alginate beads can be produced by dropping soluble sodium alginate gel drops into a calcium chloride solution. These beads have several limitations such as poor drug encapsulation due to their small size.

Osmotic delivery systems utilize osmotic pressure for controlled delivery of active agents. In these systems the release of drug(s) from osmotic systems follows zero-order kinetics. This is mainly governed by various formulation factors such as solubility, osmotic pressure of the core components, size of the delivery orifice, and nature of the rate-controlling membrane (Kunal and Mehta, 2013, International Journal of Pharmacy and Pharmaceutical Sciences, 5:1005-1013). For some of these systems the solubility of the drug is considered one of the most important parameters affecting drug release kinetics. Osmotic drug delivery systems can only deliver drugs with sufficient solubility so that the entire dose dissolves in the capsule. (about 1 mL) (Waterman et al., 2011, Journal of Controlled Release, 152: 264-269). According to Kunal et al., drugs with a density of unity and the solubility of ≤0.05 g/cm3 would be released with ≥95% zero-order kinetics. Highly water-soluble drugs would demonstrate a high release rate that would be zero-order for only a small percentage of the initial drug load. Hence, candidate drugs for osmotic delivery have water solubility in the range of 50-300 mg/ml (Kunal and Mehta, 2013, International Journal of Pharmacy and Pharmaceutical Sciences, 5:1005-1013). This issue has been addressed by osmotic capsules by Waterman K. C. and his colleagues (Waterman et al., 2011, Journal of Controlled Release, 152: 264-269). They developed an osmotic capsule that is independent of drug solubility or drug loading. They developed a capsule shell over the active tablet layer which has a hole drilled through it. This hole allows a stream of material to be extruded from the core once water imbibes through the semipermeable membrane and creates an API mixed suspension. This suspension is sufficiently viscous to suspend the API. However, it flows under the shear created by the combination of osmosis and pressure from the swelling layer to allow extrusion out of the hole in the coating.

Although osmotic capsules deliver drugs independent of drug solubility or drug load they suffer from several limitations. The rate of drug release is controlled through the thickness of the capsule shell. This dictates the water diffusion rate into the capsule core to create the resultant osmotic pressure (Waterman et al., 2011, Journal of Controlled Release, 152: 264-269). Thus, complete drug release in less than 6 hours is not feasible. The capsule thickness range is limited due to the mechanical constraints of placing two capsule together. Also, the manufacturing process needs high quality control management for:

A. Tablet manufacturing since all ingredients are in powder form.

B. Capsule orifice diameter.

C. Thickness of the capsule shell.

D. Thickness uniformity.

Applying current to a hydrogel as a mechanism to control drug release was previously studied (Kwon et al., 1991, Letters to Nature, 354: 291-293). Kwon proposed a solid matrix made with poly(ethyloxaline) and poly methacrylic acid (PMAA) as an implant. This matrix dissolves at pH 5.4 and precipitates at a lower pH. However, the procedure they used was complicated which limited its practical application.

In 1992, Yuk et al developed a composite of calcium alginate/polyacrylic acid to use it as an electric current-sensitive drug delivery system (Yuk et al., 1992, Pharmaceutical Research, 9(7):955-957). They observed a pulsatile drug release upon application of electric current. However, the way they prepared the calcium alginate composite suffered several limitations and made it difficult for practical application.

Thus, there remains a need in the art for novel methods for producing big and uniform dried alginate gel tablets, and optimized new formulations comprising various adjuvants. There also remains a need in the art for new models which can be used to formulate drug release profiles of novel calcium alginate dosage forms. There remains a need in the art for bigger, more uniform, tablet size calcium alginate dosage form that can be produced in a simple process with minimum quality control. There also remains a need in the art for tablets with a zero order release profile that can be easily adjusted by varying cross linking time and/or the concentration of the cross linking solution or by the use of additives. There also remains a need in the art for drug dosage forms that release the drug in an uniform manner regardless of the properties of the drug. There remains a need in the art for novel calcium alginate oral dosage forms which deliver drugs by electrochemical interaction, or fail-safe alginate tablets. This invention fulfils these needs.

SUMMARY OF INVENTION

In one aspect, the invention relates to a composition comprising an alginate. In one embodiment, the alginate is calcium alginate. In one embodiment, the composition further comprises a fatty acid. In one embodiment, the fatty acid is stearic acid. In another embodiment, the composition further comprises at least one stearate. In one embodiment, the at least one stearate is sodium stearate. In one embodiment, the composition further comprises ethyl cellulose. In one embodiment, the composition further comprises a drug.

In another aspect, the invention relates to a drug dosage form comprising a composition comprising an alginate. In one embodiment, the drug is selected from the group consisting of: a weak acid, a weak base, a zwitterion, and a neutral compound. In another embodiment, the drug is selected from the group consisting of ibuprofen, guaifenesin and caffeine. In one embodiment, the dosage form is a tablet. In another embodiment, the tablet is tamper resistant. In another embodiment, the dosage form is a subcutaneous insert. In one embodiment, the drug is released from the dosage form according to a delayed release profile. In one embodiment, the percentage of drug released from the dosage form is less than 20% in 8 hours. In another embodiment, the percentage of drug released from the dosage form is more than 80% in 12 hours.

In another aspect, the invention relates to a method of delivering a drug to a subject, comprising administering to the subject a drug dosage form comprising a composition comprising an alginate. In one embodiment, the delivery is oral. In another embodiment, the delivery is subcutaneous. In one embodiment, an electrode is appended to the drug dosage form. In one embodiment, the electrode is a cathode. In another embodiment, the electrode is an anode. In one embodiment, the method further comprises applying an electric current between the electrode and the medium surrounding the dosage form.

In another aspect, the invention relates to a method of making a tablet, comprising: using a basket, dipping the basket in a cross linking solution, filling the basket with a formulation comprising an alginate, and dipping the basket containing the formulation in a cross linking solution for a period of time. In one embodiment, the formulation further comprises a fatty acid. In another embodiment, the formulation further comprises a stearate. In another embodiment, the formulation further comprises ethyl cellulose. In another embodiment, the formulation further comprises a drug. In one embodiment, the release profile and lag-time for release of the drug from the tablet are controlled by controlling the period of time, controlling the concentration of the cross-linking solution, and using additives. In one embodiment, the tablet is tamper resistant.

In another aspect, the invention relates to a method of preventing extraction of a drug from a tablet by a consumer, comprising using a composition comprising an alginate to fabricate the tablet.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 3, comprising FIGS. 3A and 3B, depicts a mesh basket covered with filter paper that allows the passage of liquid from outside, which is used in the methods of the invention.

DETAILED DESCRIPTION

Figure 1:
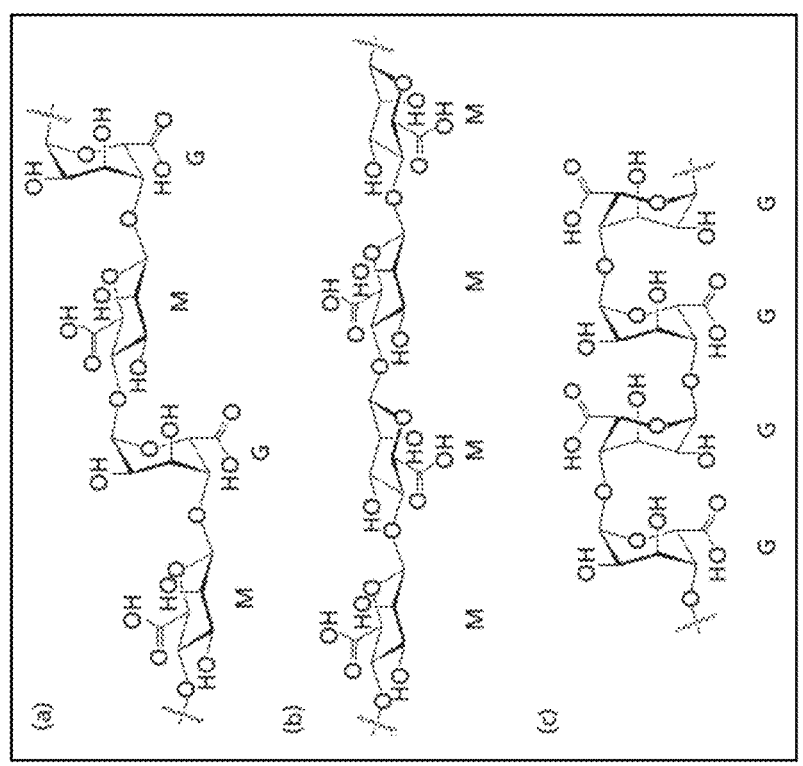
FIG. 1 depicts the chemical structures of alginates composed of block sequences of (a) MG, (b) MM and (c) GG, wherein M is b-d-mannuronic acid, and G is a-1-guluronic acid.

The invention describes compositions comprising calcium alginate, and the use thereof in making drug dosage forms. The invention also describes novel methods of molding the compositions into conventionally sized tablets, using the compositions in tablet coating, methods of describing the drug release profiles from these tablets and means of controlling the release. These methods include controlling the ingredients used for making the tablets, the cross-linking conditions, and the use of an electric current. The invention also describes the use of calcium alginate compositions in making tamper resistant tablets.

The present invention is described with reference to the attached figures, wherein like reference numerals are used throughout the figures to designate similar or equivalent elements. The figures are not drawn to scale and they are provided merely to illustrate the instant invention. Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. The present invention is not limited by the illustrated ordering of acts or events, as some acts may occur in different orders and/or concurrently with other acts or events. Furthermore, not all illustrated acts or events are required to implement a methodology in accordance with the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Definitions

The terminology used herein is for the purpose of describing particular embodiments only and is not intended to be limiting of the invention.

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

As used herein, the term "drug" refers to any bioactive agent, and the terms "drug" and "bioactive agent" are used interchangeably.

As used herein, the term "weak acid" refers to an acid chemical compound which is partially dissociated at equilibrium.

As used herein, the term "weak base" refers to a base chemical compound which is partially dissociated at equilibrium.

As used herein, the term "zwitterion" refers to a chemical compound which has one or more positive charges, and one or more negative charges, and is overall neutral.

As used herein, the term "release" refers to the transfer of a drug from a tablet into the surrounding medium, typically a fluid.

As used herein, "dosage form" and "drug dosage form" are used interchangeably and refer to the physical appearance of a formulation including a drug, when ready for administration to a patient. For example, tablets, pills, capsules, suppositories, and subcutaneous inserts are all examples of dosage forms.

As used herein, the term "tamper resistant" refers to a dosage form such as a tablet, which cannot be physically modified, for example by crushing or dissolving, by an end user, for example a consumer.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

As used herein, the term "composition" or "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary and topical administration.

As used herein, the terms "effective amount," "pharmaceutically effective amount" and "therapeutically effective amount" refer to a nontoxic but sufficient amount of an agent to provide the desired biological result. That result may be reduction and/or alleviation of the signs, symptoms, or causes of a disease, or any other desired alteration of a biological system. An appropriate therapeutic amount in any individual case may be determined by one of ordinary skill in the art using routine experimentation.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the language "pharmaceutically acceptable salt" refers to a salt of the administered compounds prepared from pharmaceutically acceptable non-toxic acids, including inorganic acids, organic acids, solvates, hydrates, or clathrates thereof. Examples of such inorganic acids are hydrochloric, hydrobromic, hydroiodic, nitric, sulfuric, phosphoric, acetic, hexafluorophosphoric, citric, gluconic, benzoic, propionic, butyric, sulfosalicylic, maleic, lauric, malic, fumaric, succinic, tartaric, amsonic, pamoic, p-toluenesulfonic, and mesylic. Appropriate organic acids may be selected, for example, from aliphatic, aromatic, carboxylic and sulfonic classes of organic acids, examples of which are formic, acetic, propionic, succinic, camphorsulfonic, citric, fumaric, gluconic, isethionic, lactic, malic, mucic, tartaric, para-toluenesulfonic, glycolic, glucuronic, maleic, furoic, glutamic, benzoic, anthranilic, salicylic, phenylacetic, mandelic, embonic (pamoic), methanesulfonic, ethanesulfonic, pantothenic, benzenesulfonic (besylate), stearic, sulfanilic, alginic, galacturonic, and the like. Furthermore, pharmaceutically acceptable salts include, by way of non-limiting example, alkaline earth metal salts (e.g., calcium or magnesium), alkali metal salts (e.g., sodium-dependent or potassium), and ammonium salts.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

As used herein, the term "safe and effective amount" refers to the quantity of a component which is sufficient to yield a desired therapeutic response without undue adverse side effects (such as toxicity, irritation, or allergic response) commensurate with a reasonable benefit/risk ratio when used in the manner of this invention. By "therapeutically effective amount" is meant an amount of a compound of the present invention effective to yield the desired therapeutic response. The specific safe and effective amount or therapeutically effective amount will vary with such factors as the particular condition being treated, the physical condition of the patient, the type of mammal or animal being treated, the duration of the treatment, the nature of concurrent therapy (if any), and the specific formulations employed and the structure of the compounds or its derivatives.

The terms "patient" "individual," and "subject" are used interchangeably herein, and refers to a mammalian subject to be treated, with human patients being preferred. In some cases, the methods of the invention find use in experimental animals, in veterinary application, and in the development of animal models for disease, including, but not limited to, rodents including mice, rats, and hamsters; and primates.

"Treatment" is an intervention performed with the intention of preventing the development or altering the pathology or symptoms of a disorder. Accordingly, "treatment" refers to both therapeutic treatment and prophylactic or preventative measures. "Treatment" may also be specified as palliative care. Those in need of treatment include those already with the disorder as well as those in which the disorder is to be prevented. In tumor (e.g., cancer) treatment, a therapeutic agent may directly decrease the pathology of tumor cells, or render the tumor cells more susceptible to treatment by other therapeutic agents, e.g., radiation and/or chemotherapy. Accordingly, "treating" or "treatment" of a state, disorder or condition includes: (1) preventing or delaying the appearance of clinical symptoms of the state, disorder or condition developing in a human or other mammal that may be afflicted with or predisposed to the state, disorder or condition but does not yet experience or display clinical or subclinical symptoms of the state, disorder or condition; (2) inhibiting the state, disorder or condition, i.e., arresting, reducing or delaying the development of the disease or a relapse thereof (in case of maintenance treatment) or at least one clinical or subclinical symptom thereof; or (3) relieving the disease, i.e., causing regression of the state, disorder or condition or at least one of its clinical or subclinical symptoms. The benefit to an individual to be treated is either statistically significant or at least perceptible to the patient or to the physician.

A "therapeutic" treatment is a treatment administered to a subject who exhibits signs of pathology, for the purpose of diminishing or eliminating those signs.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Compositions and Formulations

Figure 2:
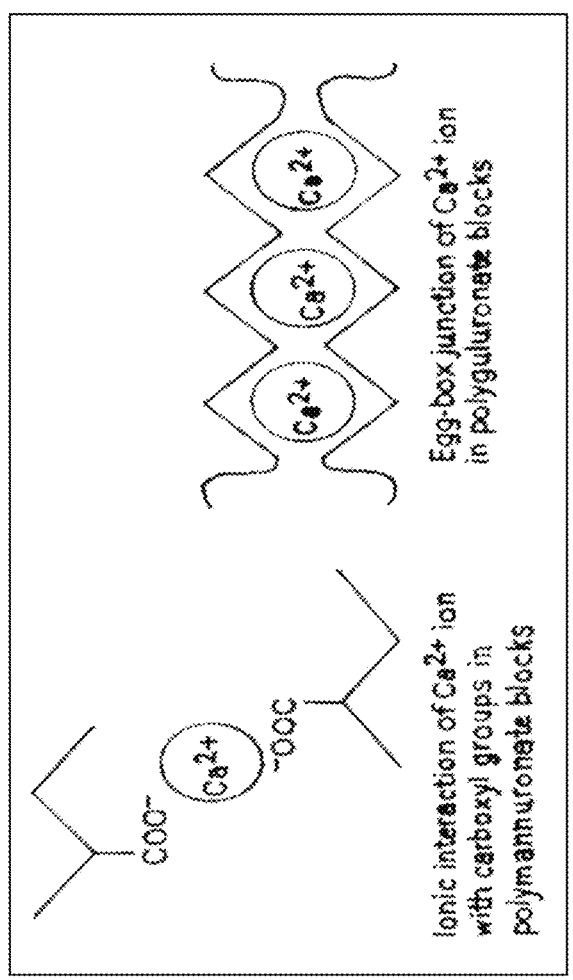
FIG. 2 depicts the bonding interactions between $Ca^{+2}$ ions and carboxyl groups in the calcium alginate beads, also known as the "egg box model."

In one aspect, the invention relates to a composition comprising an alginate. In one embodiment the alginate is calcium alginate. In another embodiment, the alginate is alginic acid. The alginate chain is made of the following regions: two homopolymeric regions of β-d-mannuronic acid (M) blocks and α-1-guluronic acid (G) blocks, interdispersed with regions of alternating structure of α-1-guluronic and β-d-mannuronic acid blocks (FIG. 1; The chemical structures of alginates composed of block sequences of (a) MG, (b) MM and (c) GG. M, b-d-mannuronic acid; G, a-1-guluronic acid). An insoluble gel composed of three-dimensional network is formed upon gelation process of alginate when blocks of guluronic acid residues interact ionically with divalent cations such as $Ca^{+2}$. This network is usually described by the egg box model (FIG. 2; Bonding interactions between $Ca^{+2}$ ions and carboxyl groups in the calcium alginate beads).

In one embodiment, the composition further includes a fatty acid, such as for example stearic acid. In another embodiment, the composition includes a stearate, such as for example sodium stearate. In another aspect, the composition further comprises ethyl cellulose. In another aspect, the composition further comprises lactose. In another aspect, the composition further comprises corn oil, or any other suitable oil. In another aspect, the composition further comprises glycerol. In another aspect, the composition further comprises cellulose, for example microcrystalline cellulose. In another aspect, the composition further comprises guarana extract. In another aspect, the composition further comprises titanium dioxide.

In one embodiment, the invention provides a formulation for a desired release of a therapeutic agent. In one aspect the composition further comprises a drug. In one embodiment, the drug is a weak acid. In another embodiment, the drug is a weak base. In another embodiment, the drug is a zwitterion. In another embodiment, the drug is a neutral compound. In some embodiments, examples of drugs included are, without being limited to, ibuprofen, guaifenesin, and caffeine. In one aspect, the composition is used for making a drug dosage form, examples of which include, but are not limited to, a tablet. In another aspect, a tablet of the invention is used by itself. In another aspect of the invention, the tablet has an electrode appended to it. In another aspect of the invention, the tablet is tamper resistant, for example cannot be crushed or dissolved. In another aspect of the invention, the tablet has a core and a coating.

In one aspect, the invention relates to the discovery that a tablet formulation has a better shape when stearic acid is added to the formulation. In some embodiments, tablets without stearic acid have an indentation on the top of the tablet. In other embodiments, the indentation does not occur when stearic acid is used in the tablet.

In one embodiment, the invention provides an oral controlled release formulation. In another embodiment, the composition of the invention is formulated for oral sustained release. However, the invention should not be limited to only oral formulations but rather encompass any forms of formulations that provide one or more of low dose and sustained release of the therapeutic agent. In one embodiment, the invention provides a subcutaneous controlled release formulation. In another embodiment, the composition of the invention is formulated for subcutaneous sustained release.

In one embodiment, the therapeutic agent may be homogeneously dispersed in the delivery system of the invention. In another embodiment, the therapeutic agent may be non-homogeneously dispersed in the delivery system of the invention. In one embodiment, the therapeutic agent may be layered in the delivery system of the invention. In some embodiments, the therapeutic agent or pharmaceutically acceptable salt thereof is present in the delivery system of the invention in an amount of about 1 mg to about 200 mg; about 1 mg to about 150 mg; about 1 mg to about 125 mg; or about 1 mg to about 100 mg. In some embodiments, the therapeutic agent or pharmaceutically acceptable salt thereof is present in the composition in an amount of about 5 mg to about 80 mg; about 10 mg to about 70 mg; about 15 mg to about 60 mg; about 40 mg to about 80 mg; about 50 mg to about 70 mg; or about 45 mg to about 60 mg. In one embodiment, the therapeutic agent or pharmaceutically acceptable salt thereof is present in the composition in an amount of about 20 mg, about 40 mg, about 60 mg, about 75 mg, about 80 mg, about 100 mg, about 120 mg, about 140 mg, about 150 mg, about 160 mg, about 175 mg, about 180 mg or about 200 mg. In one embodiment, the therapeutic agent or pharmaceutically acceptable salt thereof is present in the composition in an amount of about 2 mg. In another embodiment, the therapeutic agent or pharmaceutically acceptable salt thereof is present in the composition in an amount of about 150 mg.

In some embodiments, the sustained release delivery system is present in the composition in an amount from about 10 mg to about 420 mg; from about 25 mg to about 225 mg; from about 21 mg to about 198 mg; or from about 80 mg to about 200 mg; from about 80 mg to about 220 mg; from about 90 mg to about 210 mg; from about 100 mg to about 200 mg; from about 110 mg to about 190 mg; from about 120 mg to about 180 mg; from about 130 mg to about 170 mg; from about 140 mg to about 160 mg; from about 30 mg to about 60 mg; from about 60 mg to about 180 mg; from about 30 mg to about 180 mg, from about 75 mg to about 150 mg, from about 80 mg to about 160 mg, from about 90 mg to about 150 mg, from about 100 mg to about 140 mg, from about 110 mg to about 130 mg, from about 100 mg to about 300 mg, from about 200 mg to about 300 mg or from about 200 mg to about 250 mg. In one embodiment, the sustained release delivery system is present in the composition in an amount from about 75 mg to about 150 mg. In some embodiments, the sustained release delivery system is present in the composition in an amount of about 30 mg, about 60 mg, about 75 mg, about 80 mg, about 90 mg, about 100 mg, about 110 mg, about 112 mg, about 115 mg, about 117 mg, about 120 mg, about 125 mg, about 130 mg, about 135 mg, about 140 mg, about 145 mg, about 150 mg, about 160 mg, about 170 mg, about 180 mg, about 190 mg, about 200 mg, about 210 mg, about 220 mg, about 225 mg, about 230 mg, about 240 mg, about 250 mg, about 260 mg, about 270 mg, about 280 mg, about 300 mg, about 320 mg, about 340 mg, about 360 mg, about 380 mg, about 400 mg or about 420 mg.

In one embodiment of the invention, the compounds of the invention are administered to a patient, alone or in combination with another pharmaceutical agent, using a controlled release formulation.

In one embodiment, the controlled release formulation of a therapeutic agent is an orally administrable solid dosage formulation. Non-limiting examples of oral solid dosage formulations include tablets, capsules including a plurality of granules, sublingual tablets, powders, granules, syrups, and buccal dosage forms. In some embodiments, tablets have an enteric coating or a hydrophilic coating.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

The present invention also includes a multi-layer tablet comprising a layer providing for the delayed release of one or more compounds of the invention, and a further layer providing for the immediate release of a medication for treatment of G-protein receptor-related diseases or disorders. Using a wax/pH-sensitive polymer mix, a gastric insoluble composition may be obtained in which the active ingredient is entrapped, ensuring its delayed release.

Methods of Making

In one aspect the invention relates to various methods, such as for example methods of preparing the compositions described here, or methods of making tablets from the compositions of the invention. In one aspect, the invention describes a method of making alginate tablets, in particular drug containing alginate tablets, comprising using a mesh basket which can be filled with an alginate formulation and dipped into a cross-linking solution. In one aspect, the invention describes a method of making alginate tablets, in particular drug containing alginate tablets, comprising using a press, for example a Carver press, or a Minipress IIBD. In another one aspect, the invention describes a method of making tablets' coating, in particular tablets' coating comprising alginate. In another aspect, the invention describes a method of making a tamper resistant tablet, in particular a tamper resistant tablet comprising alginate.

In one embodiment, the method of making a composition described herein includes a multi-step approach which produces a dosage form in the size of a conventional tablet. In one embodiment, the method includes the use of a mesh basket covered with a filtering medium, for example filter paper, which allows the passage of liquid from outside. The basket size and shape determines the size and shape of the resulting formulation, for example a tablet. The openings of the mesh allows for an immediate and simultaneous contact of the cross linking solution with the outer surface of the gel from all sides. In one embodiment, the method includes wetting the basket by dipping it in the cross linking solution for a period of time. In another embodiment, the method includes using a delivery device, for example a syringe, to fill the basket with a premeasured amount of sodium alginate gel formulation. In another embodiment, the method includes soaking the basket again in the cross linking solution for a certain amount of time. In another embodiment, the method includes removing the cross linked tablets from the baskets, removing extra solution, and placing the tablets in an oven to be dried for a certain period of time.

In one embodiment, the method includes completely coating the gel in cross linking solution, which ensures that the specific shape and size inside the basket is maintained. The method offers perfect control of the amount, size, and shape of the tablet. The ability to make a larger tablet allows for a longer drug release profile than could be obtained using traditional alginate beads. The release profile and lag-time for release can be controlled by cross-linking time, the cross-linking solution concentration and by the use of additives. The described method allows for a simpler and more controlled method for producing sodium alginate solid oral dosage forms.

In another embodiment, the methods include a multi-step method of coating a tablet with a composition. In one embodiment, the method includes dipping a tablet in calcium chloride solution for a period of time, and optionally removing the extra solution. In another embodiment, the method includes dipping a tablet in an oil coating solution, for example castor oil coating solution for a period of time. In another embodiment, the method includes washing the tablet in water, for example deionized water, to remove excess coating material. In another embodiment, the method includes dipping a tablet in a calcium chloride solution for a period of time, and optionally removing the extra solution. In another embodiment, the method includes dipping a tablet in a coating, for example a cellulose coating, or more specifically a microcrystalline cellulose coating for a period of time, and optionally washing away the excess coating with water, for example deionized water. Any or all steps of the method can be optionally repeated as many times as necessary. In another embodiment, the method includes drying the tablet at a suitable temperature, for example at 35° C., for a suitable amount of time, for example 6 hours.

Methods of Use

In another aspect, the invention relates to methods of using the compositions described, such as for example methods of treatment and methods of controlling drug release from the tablets. In another aspect the invention allows for controlling the release profile and lag-time for release of the drug from an alginate tablet, by controlling the period of time for cross-linking, the concentration of the cross-linking solution, and using additives. In one aspect, the invention describes a method of releasing a drug from an alginate tablet, wherein the tablet is attached to an electrode, comprising applying an electric current between the electrode and the medium surrounding the tablet. In one aspect the electrode is a cathode, and in another aspect, the electrode is an anode.

As a non-limiting example, the invention provides controlled release formulations of a therapeutic agent including a therapeutically effective amount of a desired agent or a pharmaceutically acceptable salt thereof. In one embodiment, the controlled release formulations of the invention provide a controlled release of the drug over a longer period than observed for injectable or immediate release oral formulations (e.g., at least about 8-12 hours). In one embodiment, the controlled release formulations of the invention provide a lag-time of less than 20% release in 8 hours. In another embodiment, the controlled release formulations of the invention provide a lag-time of greater than 80% release in 12 hours. Thus, by reducing the frequency of dosing, the invention provides the potential for enhanced patient convenience. The lower dosing frequency also has the potential to provide reduced side effects because the patient may be exposed to lower peak concentrations of drug over time.

In one aspect, the present invention provides a sustained release formulation that provides a steady state plasma concentration of a compound of the invention that is sustained for a period of time. In one embodiment, the steady state plasma concentration is sustained for a period of time between 12 and 24 hours. In another embodiment, the steady state plasma concentration is sustained for about 12 hours. In another embodiment, the steady state plasma concentration is sustained for about 24 hours.

"Sustained release" or "extended release" means that the therapeutic agent or pharmaceutically acceptable salt thereof is released from the formulation at a controlled rate so that therapeutically beneficial blood levels (but below toxic levels) of the therapeutic agent or pharmaceutically acceptable salt thereof are maintained over an extended period of time. Alternatively, "sustained release" or "extended release" means that the desired pharmacologic effect is maintained over an extended period of time. In one embodiment, the sustained release is over a period of time.

The period of time may be as long as a month or more and should be a release which is longer that the same amount of agent administered in bolus form. In one embodiment of the present invention, the period of time is greater than about one day, about two days, about one week, about two weeks, about one month, about two months, and any and all ranges therebetween. In one embodiment, the period of time is between about 12 and about 24 hours. In another embodiment, the period of time is about 12 hours. In another embodiment, the period of time is about 14 hours. In another embodiment, the period of time is about 24 hours. In one embodiment, the sustained release formulation is administered once a day. In another embodiment, the sustained release formulation is administered twice a day.

In one embodiment, the formulations of the present invention may be, but are not limited to, short-term, rapid-offset, as well as controlled, for example, delayed release and pulsatile release formulations. The term delayed release is used herein in its conventional sense to refer to a drug formulation that provides for an initial release of the drug after some delay following drug administration and that mat, although not necessarily, includes a delay of from about 10 minutes up to about 24 hours. The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Dosage

Administration of the therapeutic low dose, controlled release formulations of therapeutic agent of the invention to a patient, preferably a mammal, more preferably a human, may be carried out using known procedures, at dosages and for periods of time effective to treat a disease or disorder in the patient. An effective amount of the low dose, sustained release formulations of a therapeutic agent of the invention necessary to achieve a therapeutic effect may vary according to factors such as the state of the disease or disorder in the patient; the age, sex, and weight of the patient; and the ability of the therapeutic formulation to treat a disease or disorder in the patient. Low dose, sustained release regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 1 and 5,000 mg/kg of body weight/per day. One of ordinary skill in the art would be able to study the relevant factors and make the determination regarding the effective amount of the therapeutic controlled release formulations of the invention without undue experimentation.

A suitable dose of a compound of the present invention may be in the range of from about 0.001 mg to about 5,000 mg per day, such as from about 0.1 mg to about 1,000 mg, for example, from about 1 mg to about 500 mg, such as about 5 mg to about 250 mg per day. The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

The therapeutic controlled release composition of the invention may be administered to the subject either prior to or after the onset of a disease or disorder. Further, several divided dosages, as well as staggered dosages may be administered daily or sequentially, or the dose may be continuously infused, or may be a bolus injection. Further, the dosages of the therapeutic low dose, sustained release formulations of a therapeutic agent of the invention may be proportionally increased or decreased as indicated by the exigencies of the therapeutic or prophylactic situation.

In particular, the selected dosage level depends upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well known in the medical arts.

A medical doctor, e.g., physician or veterinarian, having ordinary skill in the art may readily determine and prescribe the effective amount of the therapeutic low dose, sustained release formulations of a therapeutic agent required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the therapeutic low dose, sustained release formulations of therapeutic of the invention in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of a disease or disorder in a patient.

In one embodiment, the controlled release formulations of the invention are formulated using one or more pharmaceutically acceptable excipients or carriers. In one embodiment, the formulations of the invention comprise a therapeutically effective low dose of a desired therapeutic agent and a pharmaceutically acceptable carrier.

It is understood that the amount of compound dosed per day may be administered, in non-limiting examples, every day, every other day, every 2 days, every 3 days, every 4 days, or every 5 days. For example, with every other day administration, a therapeutic low dose, sustained release formulation of DNP of the invention may be initiated on Monday with a first subsequent low dose administered on Wednesday, a second subsequent low dose per day administered on Friday, and so on. In one embodiment, the compound is dosed at least once a day. In another embodiment, the compound is dosed at least twice a day.

In one embodiment, the controlled release composition of the invention is administered to the patient in dosages that range from one to five times per day or more. In another embodiment, the formulations of the invention are administered to the patient in range of dosages that include, but are not limited to, once every day, every two, days, every three days to once a week, and once every two weeks. It is readily apparent to one skilled in the art that the frequency of administration of the various combination compositions of the invention varies from individual to individual depending on many factors including, but not limited to, age, disease or disorder to be treated, gender, overall health, and other factors. Thus, the invention should not be construed to be limited to any particular dosage regime and the precise dosage and composition to be administered to any patient is determined by the attending physical taking all other factors about the patient into account.

In the case wherein the patient's status does improve, upon the doctor's discretion the administration of the inhibitor of the invention is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Toxicity and therapeutic efficacy of such therapeutic regimens are optionally determined in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index, which is expressed as the ratio between $LD_{50}$ and $ED_{50}$. The data obtained from cell culture assays and animal studies are optionally used in formulating a range of dosage for use in human. The dosage of such compounds lies preferably within a range of circulating concentrations that include the $ED_{50}$ with minimal toxicity. The dosage optionally varies within this range depending upon the dosage form employed and the route of administration utilized.

Once improvement of the patient's conditions has occurred, a maintenance low dose is administered if necessary. Subsequently, the dosage or the frequency of administration, or both, is reduced, as a function of the viral load, to a level at which the improved disease is retained. In one embodiment, patients require intermittent treatment on a long-term basis upon any recurrence of symptoms and/or infection.

The compounds for use in the method of the invention may be formulated in unit dosage form. The term "unit dosage form" or "dosage form," refers to physically discrete units suitable as unitary dosage for patients undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 4 or more times per day). When multiple daily doses are used, the unit dosage form may be the same or different for each dose.

In one embodiment, the present invention is directed to a packaged pharmaceutical formulation comprising a container holding a therapeutically effective amount of a formulation of the invention, alone or in combination with a second pharmaceutical agent; and instructions for using the compound to treat, prevent, or reduce one or more symptoms of a disease or disorder in a patient.

Administration

Routes of administration of any of the compositions of the invention include oral, nasal, rectal, intravaginal, parenteral, buccal, sublingual, topical, or subcutaneous. The compounds for use in the invention may be formulated for administration by any suitable route, such as for oral or parenteral, for example, transdermal, transmucosal (e.g., sublingual, lingual, (trans)buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, topical, and subcutaneous administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical and subcutaneous administration, such as for example subcutaneous inserts, and the like. It should be understood that the formulations and compositions that would be useful in the present invention are not limited to the particular formulations and compositions that are described herein.

Oral Administration

For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For oral administration, the therapeutic low dose, sustained release formulations of DNP of the invention of the invention may be in the form of tablets or capsules prepared by conventional means with pharmaceutically acceptable excipients such as binding agents (e.g., polyvinylpyrrolidone, hydroxypropylcellulose or hydroxypropylmethylcellulose); fillers (e.g., cornstarch, lactose, microcrystalline cellulose or calcium phosphate); lubricants (e.g., magnesium stearate, talc, or silica); disintegrates (e.g., sodium starch glycolate); or wetting agents (e.g., sodium lauryl sulphate). If desired, the tablets may be coated using suitable methods and coating materials such as OPADRY™ film coating systems available from Colorcon, West Point, Pa. (e.g., OPADRY™ OY Type, OYC Type, Organic Enteric OY-P Type, Aqueous Enteric OY-A Type, OY-PM Type and OPADRY™ White, 32K18400). Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid).

Granulating techniques are well known in the pharmaceutical art for modifying starting powders or other particulate materials of an active ingredient. The powders are typically mixed with a binder material into larger permanent free-flowing agglomerates or granules referred to as a "granulation." For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation generally consists in the use of materials that are solid or semi-solid at room temperature (i.e. having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e. drug) by forming a solid dispersion or solid solution.

U.S. Pat. No. 5,169,645 discloses directly compressible wax-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) melt.

Parenteral Administration

For parenteral administration, the therapeutic low dose, sustained release formulations of DNP of the invention may be formulated for injection or infusion, for example, intravenous, intramuscular or subcutaneous injection or infusion, or for administration in a bolus dose and/or continuous infusion. Suspensions, solutions or emulsions in an oily or aqueous vehicle, optionally containing other formulatory agents such as suspending, stabilizing and/or dispersing agents may be used. Subcutaneous inserts are used for subcutaneous administration.

Additional Administration Forms

Additional dosage forms of this invention include dosage forms as described in U.S. Pat. Nos. 6,340,475; 6,488,962; 6,451,808; 5,972,389; 5,582,837; and 5,007,790. Additional dosage forms of this invention also include dosage forms as described in U.S. Patent Applications Nos. 20030147952; 20030104062; 20030104053; 20030044466; 20030039688; and 20020051820. Additional dosage forms of this invention also include dosage forms as described in PCT Applications Nos. WO 03/35041; WO 03/35040; WO 03/35029; WO 03/35177; WO 03/35039; WO 02/96404; WO 02/32416; WO 01/97783; WO 01/56544; WO 01/32217; WO 98/55107; WO 98/11879; WO 97/47285; WO 93/18755; and WO 90/11757.

Those skilled in the art recognizes, or is able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction or formulation conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compositions of the present invention and practice the claimed methods. The following working examples therefore, specifically point out the preferred embodiments of the present invention, and are not to be construed as limiting in any way the remainder of the disclosure.

Example 1: A Calcium Alginate Dosage Form in the Size of a Conventional Tablet

The invention uses a four-step, novel approach which produces a dosage form in the size of a conventional tablet. This addresses the limitations related to the small size of these beads and their preparation process. The procedure utilizes a mesh basket covered with filter paper that allows the passage of liquid from outside (FIG. 3). The basket size determines the size and shape of the gel. The openings of the mesh allows for an immediate and simultaneous contact of the cross linking solution with the outer surface of the gel from all sides.

The procedure is as follows:
1. The basket is wetted by dipping it in the cross linking solution for a second.
2. Using a syringe, the basket is filled with a premeasured amount of sodium alginate gel formulation.
3. The basket is soaked again in the cross linking solution for a certain amount of time.
4. Finally, the cross linked tablets are then taken away from the baskets and wiped off extra solution and placed in an oven to be dried for 48 hours.

This method completely coats the gel in cross linking solution. This ensures that the specific shape and size inside the basket is maintained. This method offers perfect control of the amount, size, and shape of the tablet. The ability to make a larger tablet allows for a longer drug release profile than could be obtained using alginate beads. The release profile and lag-time for release can be controlled by cross-linking time, the cross-linking solution concentration and by the use of additives. The described method allows for a simpler and more controlled method for producing sodium alginate solid oral dosage forms.

Materials and Methods

Materials: potassium phosphate monobasic (99.99%), sodium hydroxide (ACS reagent, ≥97.0%), lactose monohydrate NF, stearic acid NF (Spectrum, USA), sodium stearate NF (Spectrum, USA), ethocel (DOW, USA), Avicel-PH-102 (FMC Biopolymer, USA), corn oil NF (Ruger, USA), alginic acid sodium salt (Sigma Aldrich, United Kingdom), caffeine monohydrate (MP, USA), sucrose ≥99.9%, calcium chloride dihydrate (Fisher, USA), ibuprofen. HPLC grade acetonitrile from Fischer scientific was used in preparation of mobile phase.

Analysis: an Agilent 1100 series HPLC with autosampler and dual wavelength detector was used. The mobile phase was acetonitrile to water with 0.5% formic acid (60:50 v/v). The flow rate was 1.2 mL/min and the sample injection volume was 50 μL and the wavelength of detection was 214 nm. The column used was a 150 by 4.6 mm Eclipse Plus C18 column (Agilent).

Methods: a basic hydro-gel was formulated using 1.6 g sodium alginate, 1.6 g lactose, 3 g sucrose, and 1 g ibuprofen as a model drug. Depending on the formula needed 1 g or 3.6 g stearic acid was also added to these ingredients. Using a stirrer, the dry ingredients of the previous formulations were mixed with 30 ml deionized water on a warm water bath (45° C.) until uniformly mixed. Then, 8 g of glycerol was added and mixed well until smooth and consistent gel was formed. The gel was degassed for 30 minutes to release air bubbles.

Figure 4:
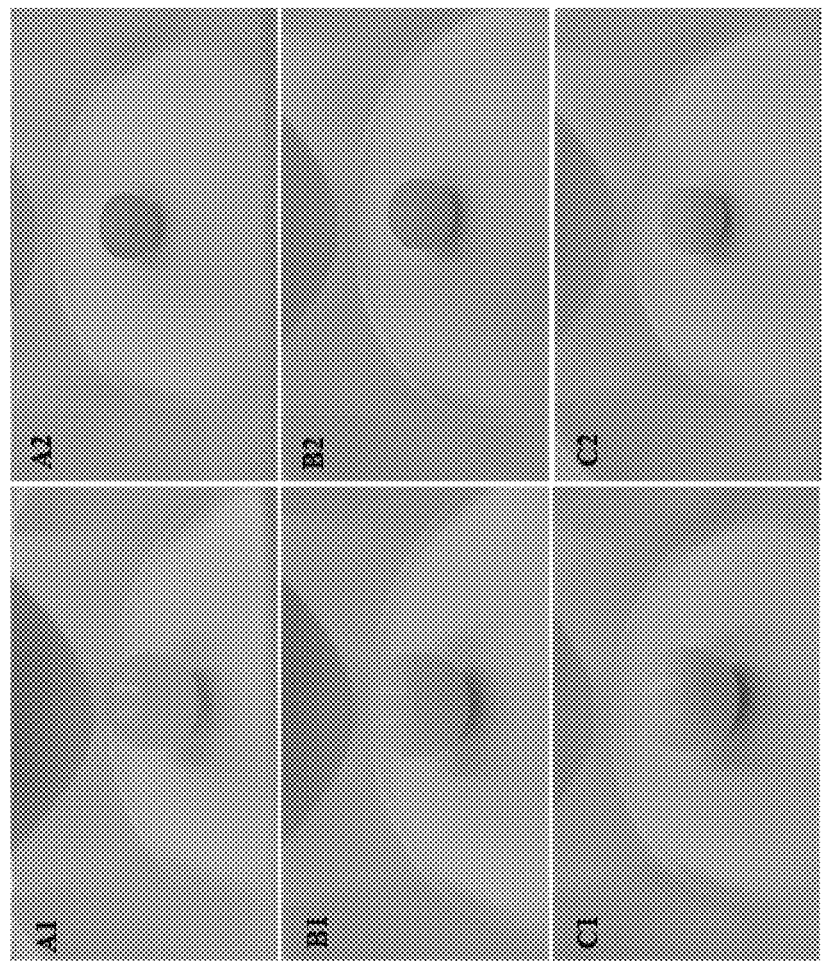
FIG. 4, comprising FIGS. A1, A2, B1, B2, C1, and C2, depicts the shape of tablets before and after drying, i.e., shapes of different formulated tablets before (1) and after (2) drying made with, 0 g stearic acid (A1 and A2), 1 g stearic acid (B1 and B2), and 3.6 g stearic acid (C1 and C2). All tablets were cross linked for 6 minutes in 1 molar calcium chloride solution.

To make the gel tablets 2 ml of the gel were withdrawn using a syringe. A basket with a 1 cm diameter was soaked momentarily in a calcium chloride solution, 2 molar or 1 molar as required; raised up and filled with gel previously withdrawn by the syringe. The basket was soaked again in the calcium chloride solution for different periods of time including: 3 minutes and 6 minutes in each of the calcium chloride solutions. Cross linked tablets were then taken away from the basket and wiped off extra solution. Finally, gel tablets were oven dried for 48 hours. FIG. 4 shows the shape of some of these tablets before and after drying, i.e., shapes of different formulated tablets before (1) and after (2) drying made with, 0 g stearic acid (A), 1 g stearic acid (B), 3.6 g stearic acid (C). All tablets were cross linked for 6 minutes in 1 molar calcium chloride solution.

Example 2: Dissolution and Recovery Studies

Figure 5:
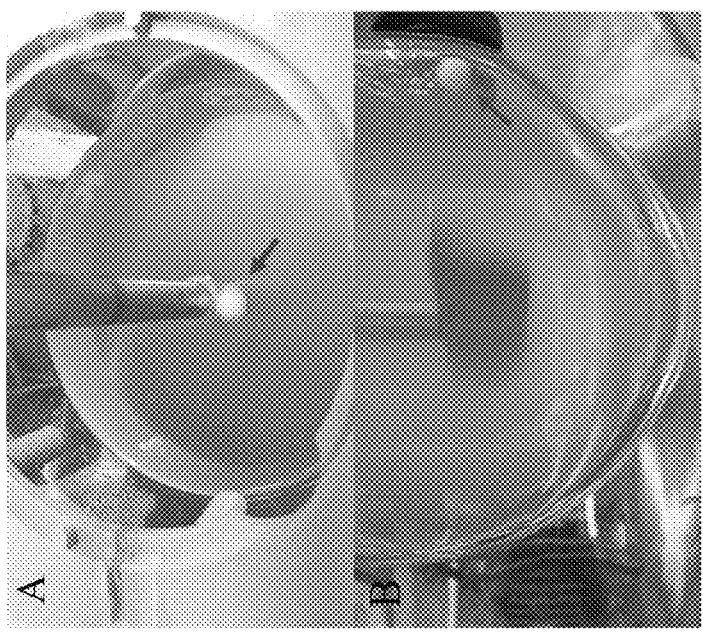
FIG. 5 depicts a dissolution apparatus.

A dissolution study was performed on each of the different tablets to determine their dissolution profiles. Dissolution USP apparatus II (Paddle) was initially used. However, it was found that the some tablets tended to float and/or hit the paddle (FIG. 5). Hence, the dissolution apparatus used was dissolution apparatus I with a rotating basket. Rotation speed was 50 RPM and the temperature was 37.0±0.5° C. The dissolution media used was 900 ml of 0.1 N hydrochloric acid in each vessel. After 2 hours the dissolution media was changed to 900 ml of standard 50 mM pH 7.2 potassium phosphate buffer. A 1 ml sample was withdrawn at each time. The samples were analyzed by HPLC.

A 24-hour recover study was performed when the drug release was not complete by 24-hours. For this study a tablet was crushed and placed in 900 ml of 100 mM potassium phosphate buffer at pH 7.2. This solution was stirred for 24 hours using a magnetic stirrer.

Figure 6:
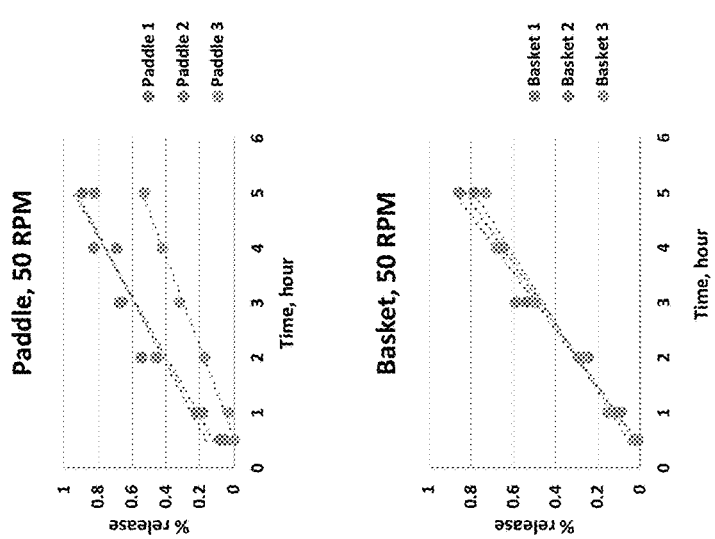
FIG. 6 is a series of charts comparing the variability in dissolution results between paddle (top), and basket (bottom).

The dissolution profiles of tablets of the same formulation showed higher variability when apparatus II was used, compared to apparatus I (FIG. 6, Comparison of variability in results between paddle (A), and basket (B)). This is because the tablets tended to float. If a tablet hit the paddle the tablet would erode more quickly. The randomness of these occurrences lead to the variability. The remaining experiments where performed using Apparatus I to reduce the variability.

When a divalent ion such as $Ca^{+2}$ is cross linked to alginate, an insoluble matrix is formed. Due to the hydration of the hydrophilic groups, calcium-alginate dry tablets gain weight. Thus, in acidic media (pH 1.2) dry calcium alginate matrices exhibit a swelling degree ranging from 89 to 172% depending on the time spent in cross linking solution (Pasparakis and Bouropoulos, 2006, International Journal of Pharmaceutics, 323:34-42v). No degradation of the tablets was observed in this media. The results showed that for all the formulations less than 5% of the drug was released in 0.1 N HCl media after two hours. However, the release of the model drug was much more significant in pH 7.2 phosphate buffer media showing a zero order release profile. It is believed that this significant release was due to the erosion of the alginate when calcium ions are detached from the alginate and reacted with the phosphate to produce calcium phosphate.

Figure 7:
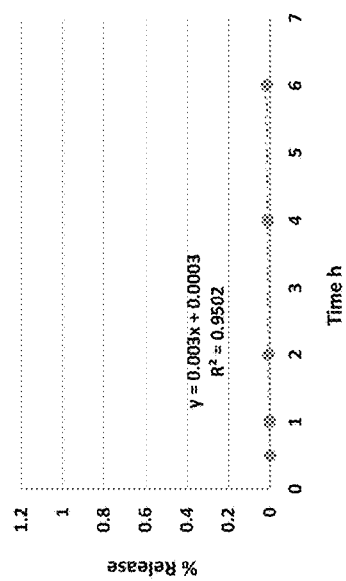
FIG. 7 is a chart depicting the release profile of ibuprofen in pH 7.2 deionized water, and showing no significant release of the drug in pH 7.2—deionized water, similar to the same behavior in acidic media.
Figure 8:
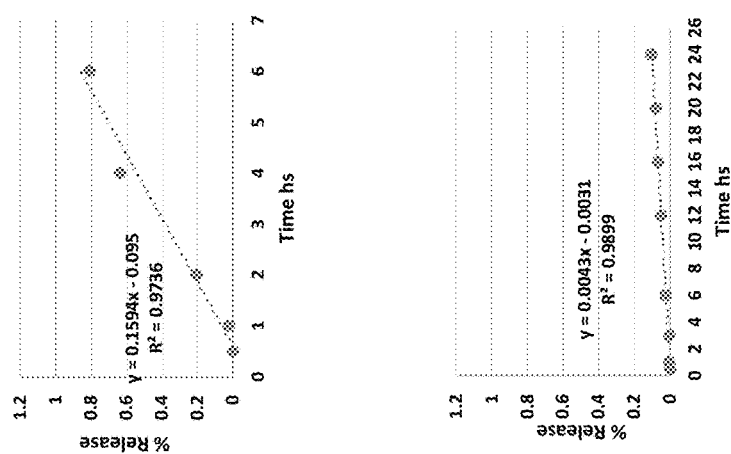
FIG. 8 is a series of charts depicting the release profile of ibuprofen from calcium alginate tablets made with 1 g stearic acid and cross linked in 1 molar $CaCl_2$ solution for 3 minutes; dissolution medium was 10 mM EDTA (top), and 10 mM EDTA+30 mM $CaCl_2$ (bottom).

In order to investigate the role of solutes and pH of the media on the erosion process, calcium alginate tablets made with same formulation were treated in different dissolution media. As shown in FIG. 7 (the release profile of ibuprofen in pH 7.2 deionized water), there was no significant release of the drug in pH 7.2—deionized water; which is similar to the same behavior in acidic media. Complete drug release profile as observed in pH 7.2 phosphate buffer was observed in the 10 mM EDTA dissolution medium. No erosion or release was observed when EDTA solution was treated with calcium chloride (FIG. 8, Release profile of ibuprofen from calcium alginate tablets made with 1 g stearic acid and cross linked in 1 molar $CaCl_2$ solution for 3 minutes; dissolution medium was 10 mM EDTA (A), and 10 mM EDTA+30 mM $CaCl_2$ (B)). These findings suggest that the erosion process of calcium alginate matrices is dependent on the presence of calcium chelating agent in the dissolution media such as phosphate or EDTA.

The dissolution of the drug from the Ca Alginate dosage form was dependent on two things. First the pH of the media had to be neutral or high. Second the media had to have the ability to complex with the Calcium in solution. This was demonstrated when the dissolution of ibuprofen in deionized water at pH 7.2 produced no drug release. The drug release at pH 7.2 in media with either EDTA or phosphate buffer was complete in 6 hours. Drug release in 0.1 N HCl was less than 5%.

These dissolution results correlated with the observation that the tablet shows no erosion in 0.1 N HCl or in pH 7.2 deionized water. The tablets did show erosion in pH 7.2 mediate with either EDTA or phosphate buffer.

Figure 9:
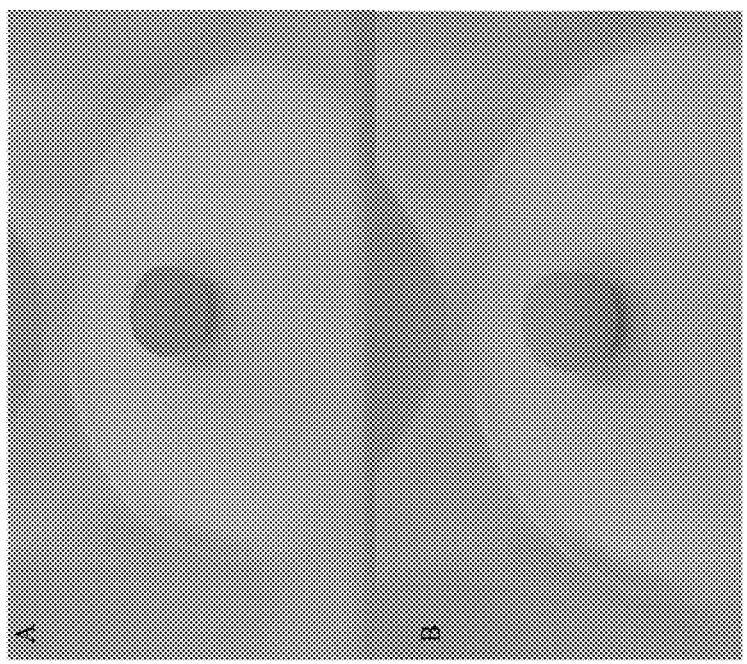
FIG. 9 is a series of photographs showing a tablet without stearic acid having an indentation on the top of the tablet (FIG. 9-A), and no indentation when stearic acid was used in the tablet (FIG. 9-B).

In early tablet formulation experiments, it was discovered that the tablets had a better shape when stearic acid was added to the formulation. Tablets without stearic acid had an indentation on the top of the tablet (FIG. 9-A). This did not occur when stearic acid was used in the tablet as shown in FIG. 9-B (Shape of tablet with indentation on the top when 0 g of stearic acid was used (A), and when 3.6 g Stearic acid was used (B)).

Example 3: Statistical Design of Experiments (DOE)

It was discovered that among the factors that have a profound effect on the drug release profile of ibuprofen were cross-linking time, concentration of calcium chloride solution, and amount of stearic acid added to the formulation. A statistical design of experiments (DOE) was performed to model the parameters to achieve different drug release profiles. The following Table 1 shows the high (+) and low (−) parameters chosen for the factor that had been used for each experiment.

TABLE 1

Factors chosen for the Design of experiment of the calcium alginate tablets

|  |  | Calcium Chloride Conc. |  | Cross Linking Time |  | Stearic Acid Amount |
|---|---|---|---|---|---|---|
| Experiment | + | 2 Molar | + | 6 minutes | + | 3.6 grams |
|  | − | 1 Molar | − | 3 minutes | − | 1 gram |
| 1 |  | + |  | + |  | + |
| 2 |  | + |  | + |  | − |
| 3 |  | + |  | − |  | + |
| 4 |  | − |  | − |  | + |
| 5 |  | − |  | + |  | − |
| 6 |  | − |  | − |  | + |
| 7 |  | − |  | − |  | − |
| 8 |  | − |  | + |  | + |

Figure 10:
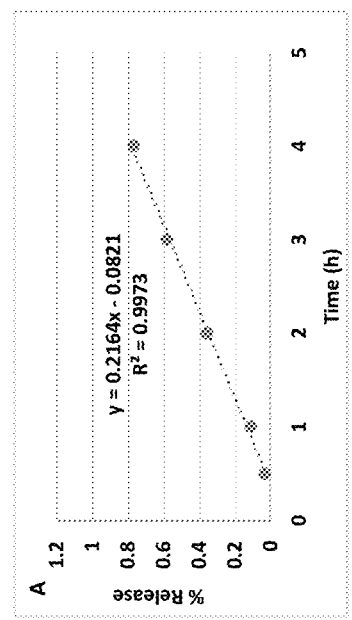
FIG. 10 is a series of charts depicting the release profile of calcium alginate tablets made with 1 g stearic acid and cross linked in 1 molar $CaCl_2$ for 3 minutes (A) and 6 minutes (B).
Figure 10:
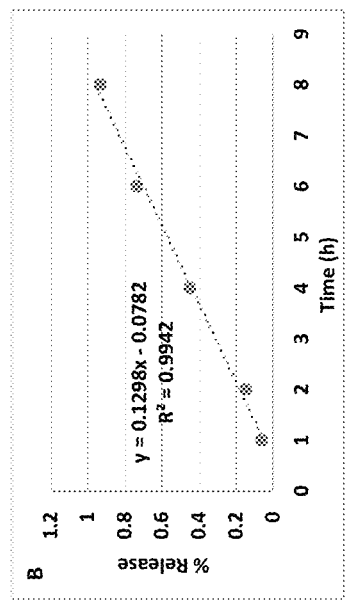
Figure 11:
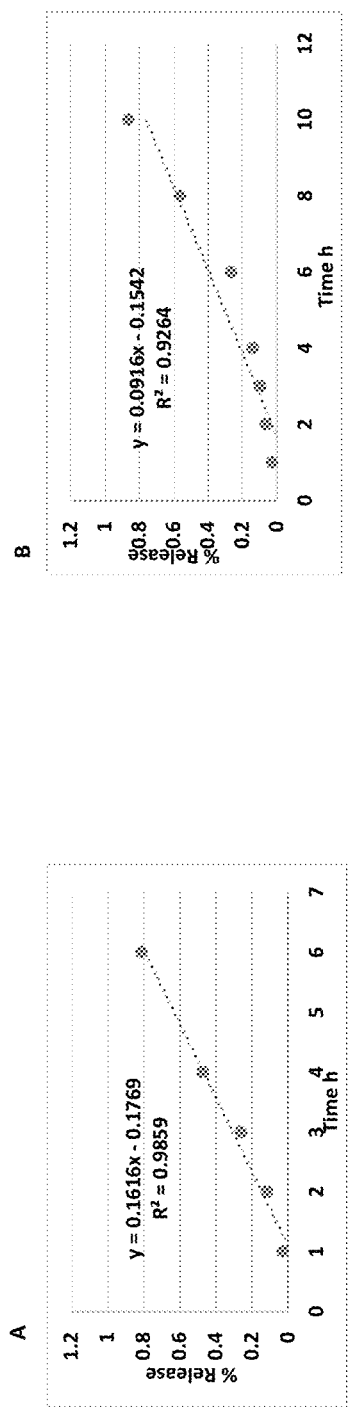
FIG. 11 is a series of charts depicting the release profile of calcium alginate tablets made with 1 g stearic acid and cross linked in 2 molar $CaCl_2$ for 3 min (A) and 6 min. (B).
Figure 12:
FIG. 12 is a series of charts depicting the release profile of calcium alginate tablets made with 3.6 g stearic acid and cross linked in 1 molar $CaCl_2$ for 3 min (A) and 6 min. (B).
Figure 13:
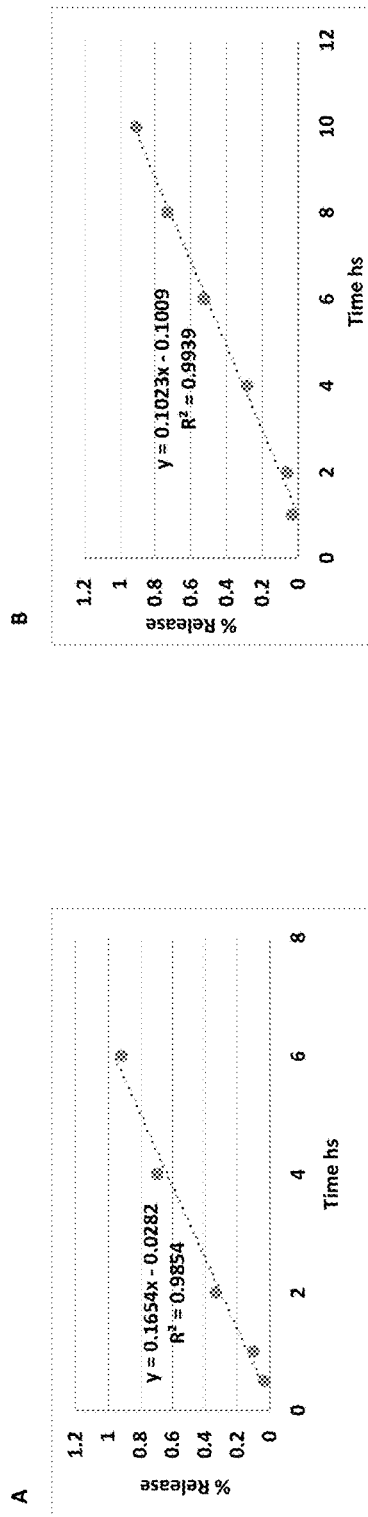
FIG. 13 is a series of charts depicting the release profile of calcium alginate tablets made with 3.6 g stearic acid and cross linked in 2 molar $CaCl_2$ for 3 min (A) and 6 min. (B).
Figure 14:
FIG. 14 is a series of charts depicting the release profile of calcium alginate tablets made with 0 g stearic acid and cross linked for 6 minutes in 1 molar $CaCl_2$ (A) and 2 molar $CaCl_2$ (B).

Release profiles of the experiments done for the DOE are shown in FIGS. 10, 11, 12, and 13. FIG. 10: Release profile of calcium alginate tablets made with 1 g stearic acid and cross linked in 1 molar $CaCl_2$ for 3 minutes (A) and 6 minutes (B). FIG. 11: Release profile of calcium alginate tablets made with 1 g stearic acid and cross linked in 2 molar $CaCl_2$ for 3 min (A) and 6 min. (B). FIG. 12: Release profile of calcium alginate tablets made with 3.6 g stearic acid and cross linked in 1 molar $CaCl_2$ for 3 min (A) and 6 min. (B). FIG. 13: Release profile of calcium alginate tablets made with 3.6 g stearic acid and cross linked in 2 molar $CaCl_2$ for 3 min (A) and 6 min. (B). Results for each experiment are summarized in Table 2. These results included the zero-order release rate ($R_0$), the time needed to release 80% of the drug (T80) and lag time (T1).

TABLE 2

Results of experiments done for the (DOE)

| $CaCl_2$ Conc. | Time | S | T1 (min) | $R_0$ | $T_{80}$ (h) |
|---|---|---|---|---|---|
| 1 | 3 | 1 | 20.3 | 0.2187 | 4 |
| 1 | 3 | 1 | 22.4 | 0.2178 | 4.04 |
| 1 | 3 | 1 | 25.8 | 0.2011 | 4.41 |
| 2 | 3 | 1 | 75.7 | 0.1639 | 6.14 |
| 2 | 3 | 1 | 55.32 | 0.1528 | 6.16 |
| 2 | 3 | 1 | 65.29 | 0.1631 | 6 |
| 1 | 3 | 3.6 | 0.57 | 0.29 | 3.66 |
| 1 | 3 | 3.6 | 1.49 | 0.221 | 3.64 |
| 1 | 3 | 3.6 | 7.6 | 0.2294 | 3.62 |
| 2 | 3 | 3.6 | 11.97 | 0.1734 | 4.81 |
| 2 | 3 | 3.6 | 10.88 | 0.1488 | 5.56 |
| 2 | 3 | 3.6 | 7.8 | 0.105 | 4.82 |
| 1 | 6 | 1 | 39.6 | 0.1318 | 6.73 |
| 1 | 6 | 1 | 37.8 | 0.1258 | 6.99 |
| 1 | 6 | 1 | 30.7 | 0.1322 | 6.56 |
| 2 | 6 | 1 | 190.2 | 0.1274 | 9.45 |
| 2 | 6 | 1 | 196.6 | 0.1236 | 9.75 |
| 2 | 6 | 1 | 204.2 | 0.1178 | 10.19 |
| 1 | 6 | 3.6 | 14.66 | 0.1702 | 4.95 |
| 1 | 6 | 3.6 | 16.5 | 0.1723 | 4.83 |
| 1 | 6 | 3.6 | 11.01 | 0.1803 | 4.62 |
| 2 | 6 | 3.6 | 61.3 | 0.0951 | 9.36 |
| 2 | 6 | 3.6 | 57.3 | 0.1033 | 8.76 |
| 2 | 6 | 3.6 | 64.67 | 0.1104 | 8.32 |

The results of the regression of the DOE data show that the Lag-Time (T1), the release rate ($R_0$) and the Time for 80% Release ($T_{80}$) could be modeled. The above data was modeled using least squares analysis using JMP version 10.0.

In the case of the zero order release rate the model had an adjusted $R^2$ of 0.96 and the residual show no trend. The model is:

$$R_0=0.003S-0.0191T-0.0474C+0.0055(T-4.5)(C-1.5)-0.0135(C-1.5)(S-2.3)-0.0074(T-4.5)(C-1.5)(S-2.3)+0.3$$

where C is the concentration of calcium chloride, T is the cross-linking time and S is the stearic acid concentration. The $R_0$ is in absolute percent per minute.

In the model of $T_{80}$ the zero order release rate is more concise. The adjusted $R^2$ is 0.98 and there is no trend in the residuals. The model is:

$$T_{80}=0.9347T+2.6C-0.43S+6.12(T-4.5)(C-1.5)-0.089(T-4.5)(S-2.3)+0.192(T-4.5)(C-1.5)(S-2.3)-0.981$$

where C is the concentration of calcium chloride, T is the cross-linking time and S is the stearic acid concentration. The $T_{80}$ is in hours. In this model the cross-linking time and the calcium chloride concentration are much more pronounced. The stearic acid concentration is more optimal at high concentration because the Lag-time causes error in the rate equation.

Figure 15:
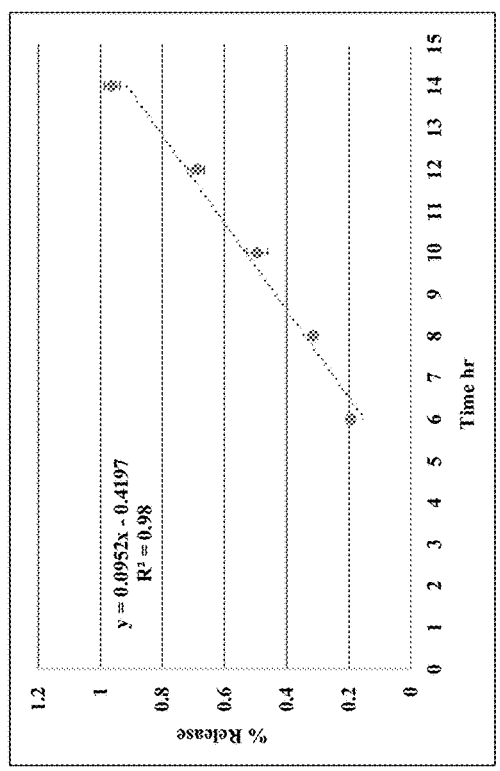
FIG. 15 is a chart depicting the release profile of ibuprofen from tablets made with 1 g stearic acid, and cross linked in 2 molar calcium chloride solution for 8 minutes.

The lag-time (T1) model has the best correlation. The adjusted $R^2$ is 0.99 and the residuals show no trend. The Model is:

$$T1=64.4C-22.37S+17.2T-28.75(C-1.5)(S-2.3)+26.4(C-1.5)(T-4.5)-5.32(S-2.3)(T-4.5)-10.04(C-1.5)(S-2.3)(T-4.5)-71.32$$

where C is the concentration of calcium chloride, T is the cross-linking time and S is the stearic acid concentration. The lag time is in minutes. This model allows for designing the drug release so that 80% release can be achieved in as little as 4 hours or as long as 12 hours. An experiment to test the model was performed where 1 gram stearic acid was used. Cross-linking time chosen was 8 minutes in 2 molar $CaCl_2$ solution. The release profile of this experiment is shown in FIG. 15 (Release profile of ibuprofen from tablets made with 1 g stearic acid, and cross linked in 2 molar calcium chloride solution for 8 minutes). Table 3 shows the comparison between the actual $T_{80}$, T1, and $R_0$ of this experiment and the ones predicted by the model. Actual value was within the prediction interval for all responses.

TABLE 3

Results of actual and predicted $T_{80}$, T1, and $R_0$

| Response | Predicted | Prediction Interval | Actual |
|---|---|---|---|
| $T_{80}$ | 12.5 hours | 13.3 to 12.1 hours | 12.8 hours |
| $R_0$ | 0.0961 | 0.1052 to 0.752 | 0.0952 |
| T1 | 284.5 min | 274.5 to 294.5 min. | 264.5 min. |

Figure 16:
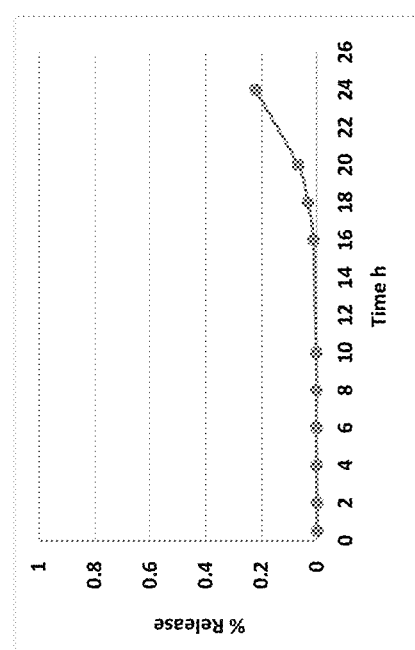
FIG. 16 is a chart depicting the release profile of calcium alginate tablets made with 1 g stearic acid, 0.8 g sucrose, and cross linked in 2 molar $CaCl_2$ solution for 20 min.

Additionally, this model also predicts that long cross-linking times can produce tablets with less than 10 percent release after 24 hours. Less than 10% of the drug was released in 20 hours dissolution period for tablets cross linked for 20 minutes in 2 M $CaCl_2$ solution made with 0.8 g of sucrose as shown in FIG. 16 (Release profile of calcium alginate tablets made with 1 g stearic acid, 0.8 g sucrose, and cross linked in 2 molar $CaCl_2$ solution for 20 min).

Faster release may be achieved using low concentrations of calcium chloride and short cross-linking times. The effect this has on the tablet morphology is not known at this time.

Example 4: Making Different Shapes

Figure 17:
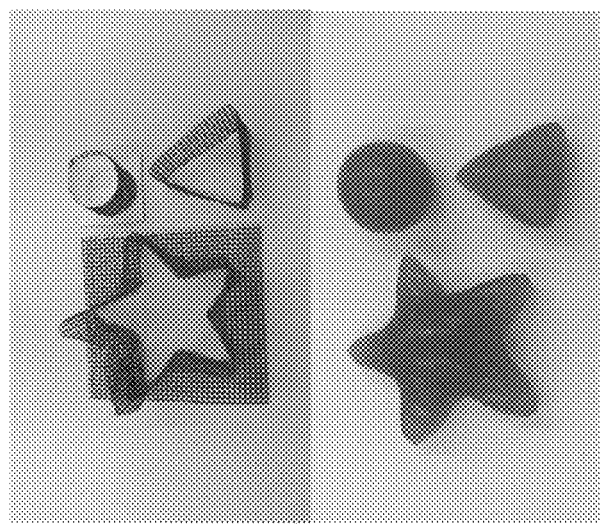
FIG. 17 is a photograph depicting the mesh basket allowing for making different shapes by molding sodium alginate.

The novel process used to mold sodium alginate in calcium chloride solution can be also applied for food production. The mesh basket allows for making different shapes as shown in FIG. 17 (different shapes of mesh baskets used to mold sodium alginate).

Example 5: Lowering Drug Loss During the Cross-Linking Process and in the Acid Stage Residence Time Materials: Lactose (monohydrate N.F, Drug and Chemical CO., INC, USA), glycerol (Fisher, USA), stearic acid (N.F, Spectrum, USA), alginic acid sodium salt (Sigma Aldrich, United Kingdom), sucrose (≥99.9%, Fisher, USA), calcium chloride (Fluka, Germany), potassium phosphate monobasic (Sigma Aldrich, USA), sodium stearate, ethyl cellulose, ibuprofen (Spectrum, USA), benzoic acid, guaifenesin, and caffeine as model drugs, HPLC grade acetonitrile from Fischer scientific was used in preparation of the mobile phase.

HPLC analysis: an Agilent 1100 series HPLC with auto-sampler and dual wavelength detector was used. The mobile phase was acetonitrile to water with 0.5% formic acid (60:50 v/v). Table 4 shows the analysis conditions used for each model drug used.

TABLE 4

Analysis condition used for each model drug used in the study

| Model drug | Flow rate ml/min. | Wave length | Injection volume (μg) |
|---|---|---|---|
| Ibuprofen | 1.2 | 214 | 50 |
| Benzoic acid | 1 | 220 | 5 |
| Guaifenesin | 1 | 276 | 20 |
| Caffeine | 1 | 275 | 20 |

Methods: different formulations were developed. Table 5 shows a summary of the ingredients used in each of these formulations and the parameters needed for the fabricating each one of these formulations. The ingredients of all the formulations were mixed with deionized water at room temperature. The basket method described in chapter two was used to fabricate the tablets. 2 or 1.5 ml of the gel was dispensed into the basket as indicated. All the tablets were air dried at room temperature for 36 hours.

For formulation D, 3 g of stearic acid was mixed with 1 g of guaifenesin and melted at 50 C using a water bath. The melted mixture was cooled down and then crushed and sieved in a #50 mesh. The sieved mixture was mixed with the other ingredients of the formula and finally fabricated into a tablet using the basket method.

For formulation K, 1 g of ibuprofen, benzoic acid, guaifenesin, or caffeine were used as model drugs. Ethyl cellulose was sieved in #50 mesh and mixed with the other ingredients as indicated. The gel was very thick. A different procedure was used to formulate the gel and fabricate the tablets.

The procedure was as follows:
A. Alginate, sodium stearate and model drug were mixed together and then added to water while stirring with a magnetic stirrer at room temperature. When the gel was too thick for the magnetic stirrer the gel was mixed by hand using a stirring-rod.
B. Once all alginate was dissolved and all ingredients were uniformly mixed, stearic acid was added while mixing.
C. Ethyl cellulose was added and blended until a consistent gel was formed.
D. Gel was placed in a sonicating-bath to release gas bubbles.
E. To make tablets, the gel was first withdrawn into a 5 ml syringe and then transferred into a 3 ml syringe to ensure release of any entrapped bubbles in the gel.
F. 1.5 ml of gel was filled in the basket device and soaked in 0.5M $CaCl_2$ for 3 minutes, washed with deionized water, and dried at room temperature for 36 hours.

TABLE 5 ingredients used for each formula and other parameters including: Cross-linking Time, CaCl$_2$ Molarity, and washing in DI water

| Formula | Ingredients | Cross-linking Time | CaCl$_2$ Molarity | Washing in DI water | Gel amount |
|---|---|---|---|---|---|
| A | 2 g starch, 3 g stearic acid, 1.6 g sodium alginate, 30 ml water. | 3 minutes | 1 molar | No | 2 ml |
| B | 2 g starch, 3 g stearic acid, 1.6 g sodium alginate, 30 ml water. | 3 minutes | 0.5 molar | Yes | 2 ml |
| C | 1 g microcrystalline cellulose, 3 g stearic acid, 1.6 g sodium, 30 ml water. | 3 minutes | 0.5 molar | Yes | 2 ml |
| D | 6 g ethyl cellulose, 3 g stearic acid, 0.5 g sodium stearate, 1.6 g sodium alginate, 30 ml water. | 3 minutes | 0.5 molar | Yes | 1.5 ml |
| E | 8 g starch, 0.5 sodium stearate, 3 g stearic acid, 1.6 g sodium alginate, 8 g ethyl cellulose, 30 ml water. | 3 minutes | 0.5 molar | Yes | 1.5 ml |
| F | 3 g starch, 3.2 g sodium alginate, 2 g stearic acid, 0.5 g sodium stearate, 30 ml water. | 3 minutes | 0.5 molar | Yes | 1.5 ml |
| G | 6 g ethyl cellulose, 2 g sodium alginate, 0.5 g sodium stearate, 3 g stearic acid, 30 ml water. | 3 minutes | 0.5 molar | Yes | 1.5 ml |
| H | 6 g ethyl cellulose, 3 g stearic acid, 0.5 g sodium stearate, 1.6 g sodium alginate, 30 ml water. | 3 minutes | 0.5 molar | Yes | 1.5 ml |
| I | 6 g ethyl cellulose, 3 g sodium alginate, 0.5 g sodium stearate, 3 g stearic acid, 30 ml water. | 3 minutes | 0.5 molar | Yes | 1.5 ml |
| J | 1 g K4K HPMC, 1.6 g sodium alginate, 3 g stearic acid, 0.5 g sodium stearate, 6 g ethyl cellulose 30 ml water. | 3 minutes | 0.5 molar | Yes | 1.5 ml |
| K | 6 g ethyl cellulose, 3.5 g sodium alginate, 3 g stearic acid, 0.5 g sodium stearate, 33 ml water. | 3 minutes | 0.5 molar | Yes | 1.5 ml |

Figure 18:
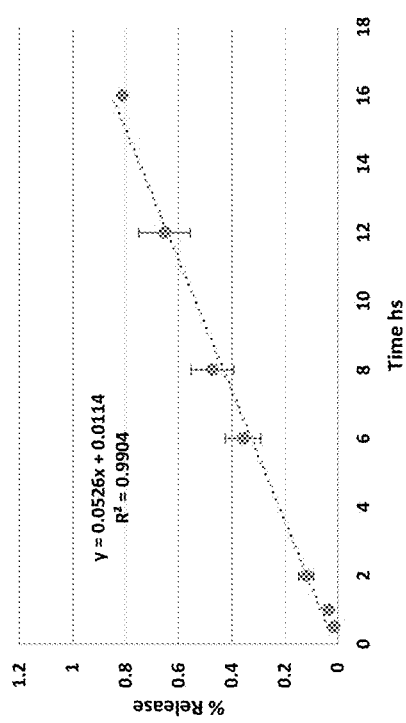
FIG. 18 is a chart depicting the release profile of benzoic acid tablets in pH 7.2 phosphate buffer; the tablets were made with: 2 g starch, 3 g stearic acid, 1.6 g sodium alginate, 30 ml water, and cross-linked in 1 molar $CaCl_2$ solution for 3 minutes, and were pretreated in 0.1 N HCl for two hours prior to treatment in the pH 7.2 phosphate buffer.

It was found that the previous formulations used for the model were not successful in retaining smaller molecular weight weak acids such as benzoic acid. Results showed that more than 30% of benzoic acid was lost during the cross-linking process alone. Also, more than 30% of the drug load was released during the residence time of the tablet in the acid stage. Apparently, using glycerol as well as lactose and sucrose in the previous formulations lead to the release of benzoic acid in a faster manner compared to ibuprofen. This is most likely caused by the increased solubility of benzoic acid in an acid environment compared to ibuprofen. Hence, a different formulations was needed. The first formulation was formulation A in table 8. This formulation didn't have sucrose, lactose or glycerol. An insignificant amount of benzoic acid was released during the cross-linking process. Only about 14% was released after two hours residence time in the acid stage. The T$_{80}$ was about 16 hours and the drug release followed zero-order kinetics (FIG. 18; Release profile of benzoic acid tablets in pH 7.2 phosphate buffer. Tablets were made with: 2 g starch, 3 g stearic acid, 1.6 g sodium alginate, 30 ml water, and cross-linked in 1 molar CaCl$_2$ solution for 3 minutes. Tablets were pretreated in 0.1 N HCl for two hours prior to treatment in the pH 7.2 phosphate buffer).

Figure 19:
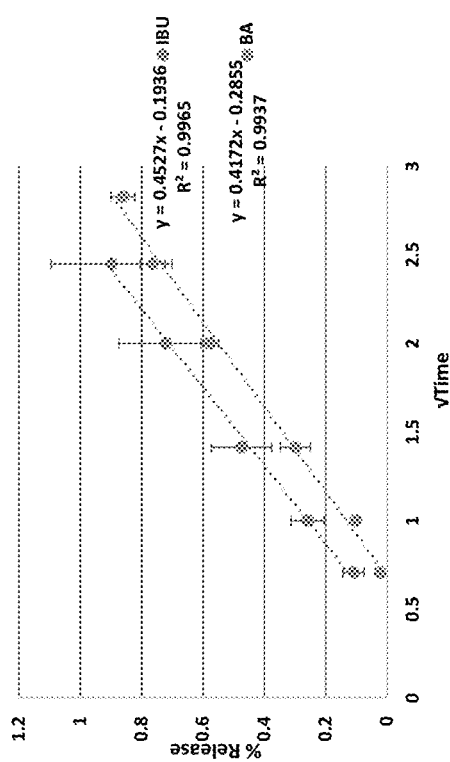
FIG. 19 is a chart depicting the release profile of benzoic acid (BA) and ibuprofen (IBU) in the buffer stage; the tablets were made with formulation B: 2 g starch, 3 g stearic acid, 1.6 g sodium alginate, 30 ml water, and cross-linked in 0.5 molar $CaCl_2$ solution for 3 minutes and cross-linked in 0.5 molar $CaCl_2$ solution for 3 minutes, and were pretreated in 0.1 N HCl for two hours prior to treatment in the pH 7.2 phosphate buffer. $T_{80}$ of ibuprofen was 4.8 hours while for benzoic acid it was 6.76 hours.

Formulation B was made as a comparator. The drug release of this benzoic acid formulation was compared to an identical formulation of ibuprofen. Tablets of ibuprofen and benzoic acid were cross-linked in 0.5 molar CaCl$_2$ solution for 3 minutes. Release profiles of both drugs followed square root of time kinetics as shown in FIG. 19 (Release profile of benzoic acid (BA) and ibuprofen (IBU) in the buffer stage. Tablets were made with formulation B: 2 g starch, 3 g stearic acid, 1.6 g sodium alginate, 30 ml water, and cross-linked in 0.5 molar CaCl$_2$ solution for 3 minutes and cross-linked in 0.5 molar CaCl$_2$ solution for 3 minutes. Tablets were pretreated in 0.1 N HCl for two hours prior to treatment in the pH 7.2 phosphate buffer). T$_{80}$ of ibuprofen was 4.8 hours while for benzoic acid it was 6.76 hours.

Figure 20:
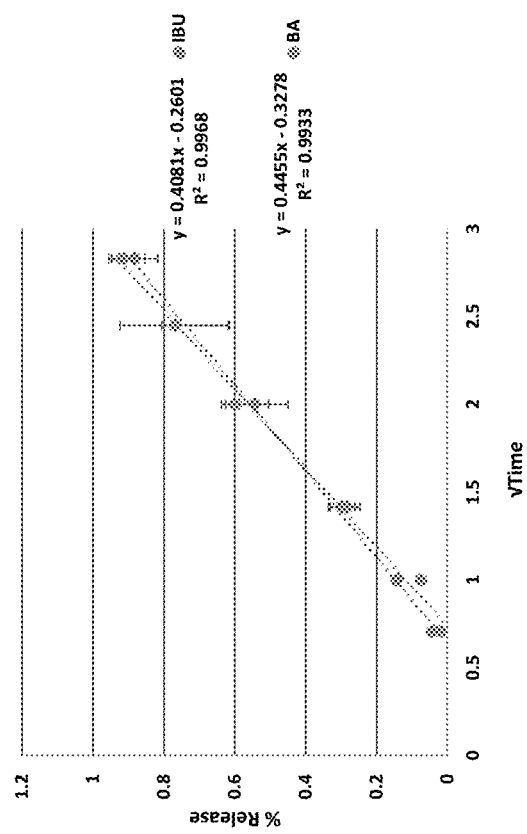
FIG. 20 is a chart depicting the release profile of benzoic acid (BA) and ibuprofen (IBU) in the buffer stage; tablets were made with formulation C: 1 g microcrystalline cellulose, 3 g stearic acid, 1.6 g sodium, 30 ml water, and were pretreated in 0.1 N HCl for two hours prior to treatment in the pH 7.2 phosphate buffer. $T_{80S}$ were 6.71 and 6.4 hours for ibuprofen and benzoic acid respectively.

Microcrystalline cellulose was used besides the other ingredients listed in table 8 for formulation C. This formulation was designed to provide a more uniform drug release profile of both benzoic acid and ibuprofen. It was found that release profiles for Ibuprofen and benzoic acid were very close and followed square root of time kinetics (FIG. 20: Release profile of benzoic acid (BA) and ibuprofen (IBU) in the buffer stage. Tablets were made with formulation C: 1 g microcrystalline cellulose, 3 g stearic acid, 1.6 g sodium, 30 ml water. Tablets were pretreated in 0.1 N HCl for two hours prior to treatment in the pH 7.2 phosphate buffer). T$_{80S}$ were 6.71 and 6.4 hours for ibuprofen and benzoic acid respectively. However, it was found that about 18% of benzoic acid was released in the acid stage after two hours.

Formulation C contained guaifenesin. Guaifenesin is a highly soluble drug (Mani et al., 2003, Pharmaceutical Development and Technology, (4):385-396). This formulation was not successful in retaining guaifenesin during the cross-linking process nor in the acid treatment stage. Hence, different formulations were developed. Criteria for these formulation to be successful was to release less than 25% of guaifenesin in the acid stage. Table 6 shows the percentage of guaifenesin released in the acid stage after two hours for each formulation; D to K.

TABLE 6

% release of guaifenesin in the acid stage for different formulations

| Formula | Ingredients | Guaifenesin % release in the acid stage |
|---|---|---|
| D | 6 g ethyl cellulose, 3 g stearic acid, 0.5 g sodium stearate, 1.6 g sodium alginate, 30 ml water. | 28 |
| E | 8 g starch, 0.5 sodium stearate, 3 g stearic acid, 1.6 g sodium alginate, 8 g ethyl cellulose, 30 ml water. | 30 |
| F | 3 g starch, 3.2 g sodium alginate, 2 g stearic acid, 0.5 g sodium stearate, 30 ml water. | 28 |
| G | 6 g ethyl cellulose, 2 g sodium alginate, 0.5 g sodium stearate, 3 g stearic acid, 30 ml water. | 27 |
| H | 6 g ethyl cellulose, 3 g stearic acid, 0.5 g sodium stearate, 1.6 g sodium alginate, 30 ml water. | 27 |
| I | 6 g ethyl cellulose, 3 g sodium alginate, 0.5 g sodium stearate, 3 g stearic acid, 30 ml water. | 43 |
| J | 1 g K4K HPMC, 1.6 g sodium alginate, 3 g stearic acid, 0.5 g sodium stearate, 6 g ethyl cellulose 30 ml water. | 29 |
| K | 6 g ethyl cellulose, 3.5 g sodium alginate, 3 g stearic acid, 0.5 g sodium stearate, 33 ml water. | 17 |

Formula K was the only formulation among the previous formulations that had the ability to release less than 20% of guaifenesin in the acid stage. Hence, this formula was used to test different kind of model drugs to test how similar the release profiles are. These drugs were: ibuprofen, caffeine, and benzoic acid.

Figure 21:
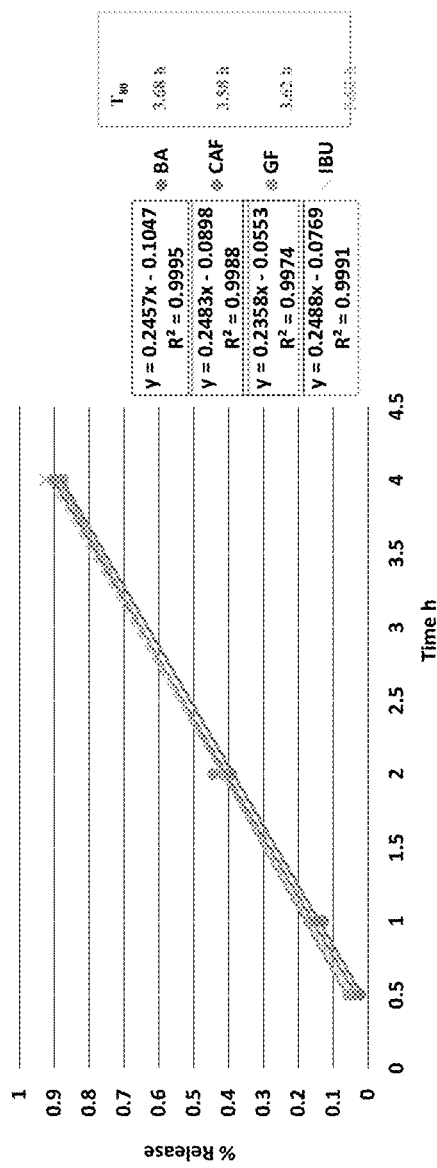
FIG. 21 is a chart depicting the release profiles and $T_{80S}$ of all the model drugs in the buffer stage; tablets were made with formulation K: 6 g ethyl cellulose, 3.5 g sodium alginate, 3 g stearic acid, 0.5 g sodium stearate, 33 ml water, where BA: Benzoic acid, CAF: Caffeine, GF: Guaifenesin, IBU: Ibuprofen, and were pretreated in 0.1 N HCl for two hours prior to treatment in the pH 7.2 phosphate buffer.

FIG. 21 (Release profiles of all the drugs in the buffer stage. Tablets were made with formulation K: 6 g ethyl cellulose, 3.5 g sodium alginate, 3 g stearic acid, 0.5 g sodium stearate, 33 ml water, where; BA: Benzoic acid, CAF: Caffeine, GF: Guaifenesin, IBU: Ibuprofen. Tablets were pretreated in 0.1 N HCl for two hours prior to treatment in the pH 7.2 phosphate buffer) shows the release profiles and T$_{80S}$ of all the model drugs. Formula K could be totally erosion based formula since it produced a uniform release rate for all the drugs used. The release kinetics were zero-order which supports an erosion-based system. Regardless of the properties of the model drugs; such as solubility or molecular weight, release profiles were very similar. In addition, less than 20% of the drugs were released in the acid stage after two hours.

Table 7 shows the percentage of amount released of these drugs after two hours in the acid stage.

TABLE 7 percent release of different drugs in the acid stage when formulation K: 6 g ethyl cellulose, 3.5 g sodium alginate, 3 g stearic acid, 0.5 g sodium stearate, 33 ml water; was used

| Drug | % released in acid stage |
|---|---|
| Ibuprofen | <1% |
| Benzoic acid | 7% |
| Guaifenesin | 17% |
| Caffeine | 18% |

Figure 22:
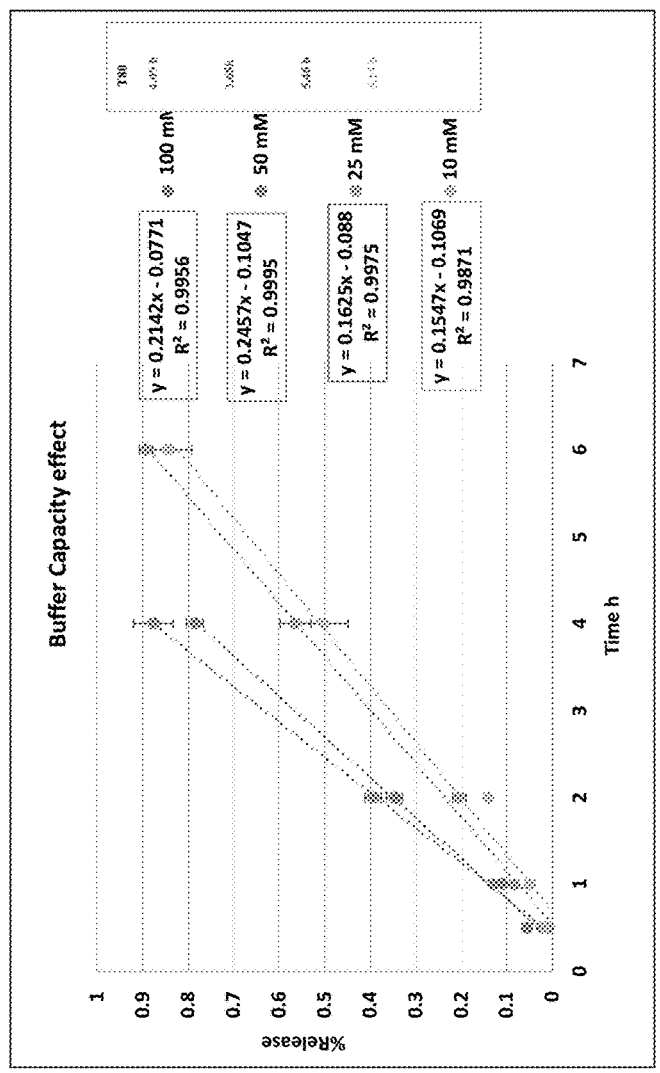
FIG. 22 is a chart showing the release profile of benzoic acid when 100, 50, 25 and 10 mM phosphate buffer were used in the dissolution media at pH 7.2, and depicting the effect of buffer capacity on the release of benzoic acid in the buffer stage; tablets were made with formulation K: 6 g ethyl cellulose, 3.5 g sodium alginate, 3 g stearic acid, 0.5 g sodium stearate, 33 ml water, and were pretreated in 0.1 N HCl for two hours prior to treatment in the pH 7.2 phosphate buffer.

Release profiles of the tablets were investigated in different buffer capacities and pH values. The tablets were pretreated in the acid stage for two hours before transferring them to the buffer stage. FIG. 22 (Effect on buffer capacity on the release of benzoic acid in the buffer stage. Tablets were made with formulation K: 6 g ethyl cellulose, 3.5 g sodium alginate, 3 g stearic acid, 0.5 g sodium stearate, 33 ml water. Tablets were pretreated in 0.1 N HCl for two hours prior to treatment in the pH 7.2 phosphate buffer) shows the release profile of benzoic acid when 100, 50, 25 and 10 mM phosphate buffer were used in the dissolution media at pH 7.2. It was found that lower buffer capacity resulted in a slower erosion rate and hence a slower drug release. On the other hand, higher buffer capacity had minimum effect on the release rate. These results show that the dilution effect of the buffer reduces inter-ionic distance which may reduce interaction between calcium ions and phosphate species (Pillay and Fassihi, 1999, Journal of Controlled Release, 59:229-242). Hence, high buffer concentration should be maintained.

Figure 23:
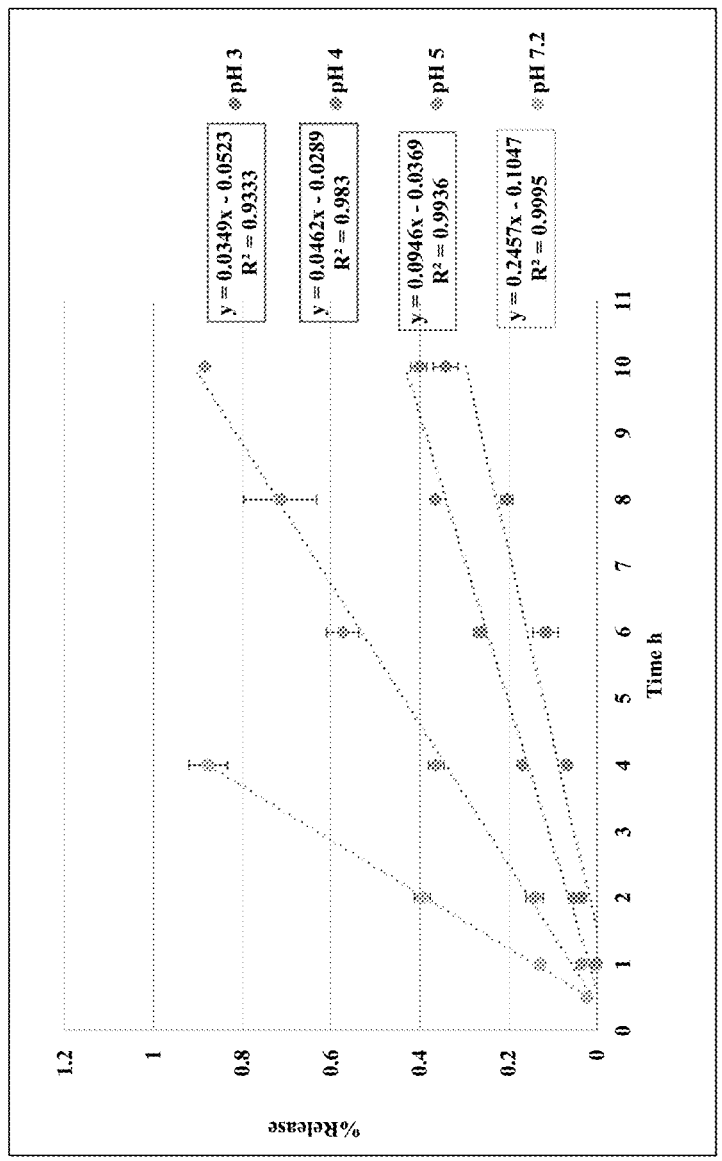
FIG. 23 is a chart showing the effect of pH of the buffer on the release profile of benzoic acid, and depicting the effect of pH on the release profile of benzoic acid in the buffer stage; tablets were made with formulation K: 6 g ethyl cellulose, 3.5 g sodium alginate, 3 g stearic acid, 0.5 g sodium stearate, 33 ml water, and were pretreated in 0.1 N HCl for two hours prior to treatment in the pH 7.2 phosphate buffer.

FIG. 23 (Effect of pH on the release profile of benzoic acid in the buffer stage. Tablets were made with formulation K: 6 g ethyl cellulose, 3.5 g sodium alginate, 3 g stearic acid, 0.5 g sodium stearate, 33 ml water. Tablets were pretreated in 0.1 N HCl for two hours prior to treatment in the pH 7.2 phosphate buffer) shows the effect of pH of the buffer on the release profile of benzoic acid. The pH of the solution is a critical parameter controlling the solubility of alginic acid. Carboxyl groups of both mannuronic acid (pKa=3.38) and guluronic acid (pKa=3.65) can be protonated by addition of inorganic acids (Rehm, 2009, Alginates: Biology and Applications, Springer-Verlag). Hence, no erosion was detected at pH 3 and pH 4 (Drug was released via diffusion). At pH 5, tablets started to erode but at a slower rate compared to pH 7.2.

Previously, the effect of the pH of the solution to pretreat alginate gel tablets for two hours was investigated. Pretreatment of the tablets in deionized water resulted in a higher T$_{80}$ compared to tablets pretreated 0.1 N HCl.

The previous results suggest that for a uniform and consistent erosion of calcium alginate tablets, it is recommended that these tablets should be coated to reduce the effect of acid-base changes in the stomach. Also, tablets should be given after meals to assure high buffer capacity and neutral pH in the intestines.

Figure 24:
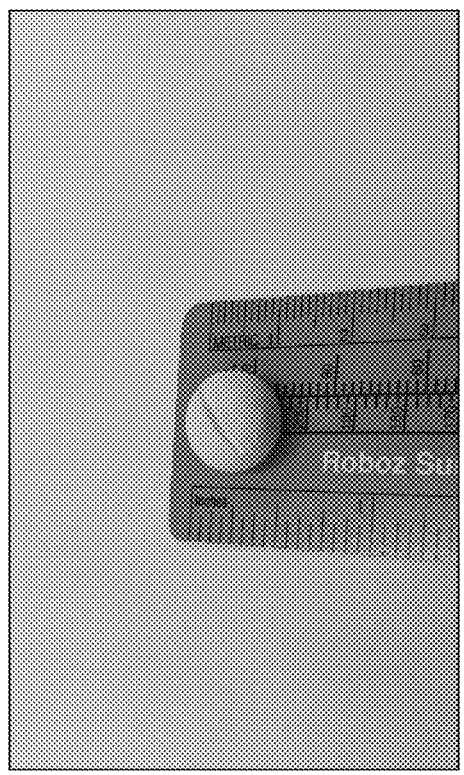
FIG. 24 is a photograph depicting a tablet made with formulation 5 with an imprint at the center.

Another feature of tablets made with formulation 5 is the ability to imprint on them as shown in FIG. 24 (Tablet made with formulation 5 with an imprint at the center).

Alginate solution composition has a deep effect on the encapsulation efficiency and the release profile of the model drug. Addition of the hydrophilic ingredients such as glycerol, sucrose and lactose resulted in low encapsulation of low molecular size and highly soluble drugs. Ethyl cellulose, a highly hydrophobic excipient, was used. It resulted in low drug loss during the cross-linking process and in the acid stage residence time. High thickness of the gel due to the addition of high amount of alginate also helped in decreasing the drug loss in the cross-linking solution. Uniform release rate was achieved with the addition of appropriate amounts of alginate, ethyl cellulose, and stearic acid. Regardless of the properties of the drug used in the formula, release rate was the same.

Example 6: Application of Electric Current on Fail-Safe Alginate Gel Tablets

Materials: zinc wire (1.0 mm diameter, extruded, 99.9%, Sigma Aldrich, USA), Sodium chloride (Fisher Scientific), Citric acid (Sigma Aldrich), zinc sulfate (Fisher), Sodium Di-hydrogen phosphate (Sigma Aldrich), ibuprofen (Millipore 1000 mw cut-off membranes, Ionotophoresis side-by side diffusion cells with 9 mm diameter opening were obtained from PermeGear. The current clamps with PC control were provided by NuPathe, Inc. The temperature controller was from Henke.

Figure 25:
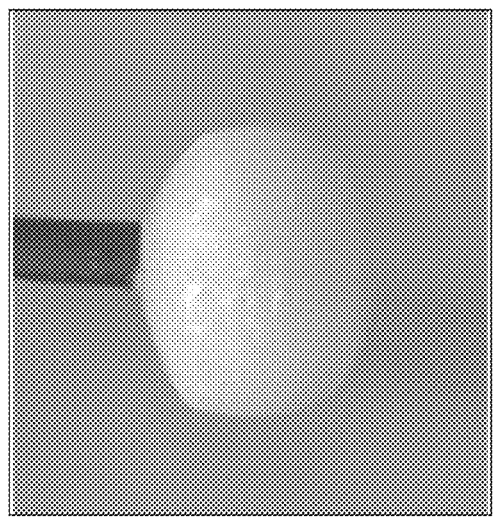
FIG. 25 is a photograph depicting an electrolytic tablet with isolated zinc wire; the photograph shows the electric fail safe tablet after drying.

Methods: the fail-safe tablet was used as the matrix for the electrolytic tablet. The ingredients for the formulation of this tablet included: 0.8 g sucrose, 1.6 g lactose, 1.6 g alginic acid, 8 g glycerol, 1 g ibuprofen and 30 ml of water. The water was heated on a 45° C. water bath. All the other ingredients except for the glycerol were mixed and added to the warm water gradually while stirring. Stirring continued until all the ingredients were homogenously mixed. Glycerol was added and mixed until solution is uniformly mixed. Solution was degassed in a sonicator to release gas bubbles. 2 ml of the solution was withdrawn with a 5 ml syringe and dispensed in the basket devise. An isolated zinc wire with a coil at one end was embedded inside this gel formulation before cross-linking took place. The dispensed gel was cross-linked in 2 molar calcium chloride solution for 20 minutes. Tablet was then removed from the basket and extra solution was removed by wiping. Finally, gel tablets were oven dried for 18 hours at 50° C. FIG. 25 (Electrolytic tablet with isolated zinc wire) shows the electric fail safe tablet after drying.

Figure 26:
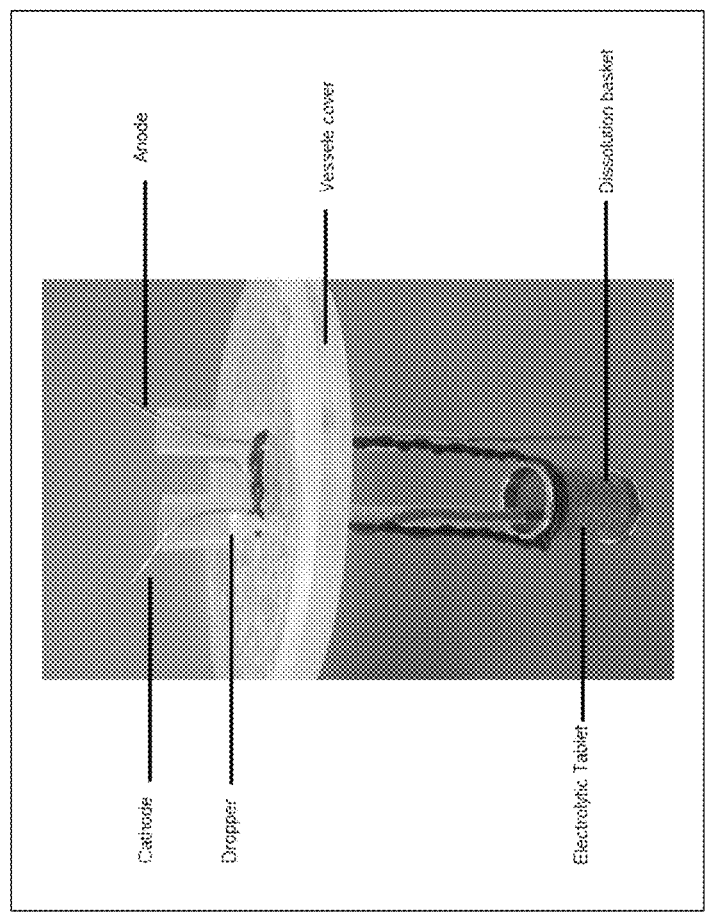
FIG. 26 is a photograph depicting the experimental set-up showing electrodes where the cathode is placed in the tablet and the anode is placed in dissolution medium bath.

FIG. 26 (Experimental set-up showing electrodes where the cathode is placed in the tablet and the anode is placed in dissolution medium) shows the experimental set-up used for placing the tablet in the dissolution bath. Apparatus II was used for the dissolution study at 50 RPM and 37° C. temperature. The dissolution media used was 900 ml of 0.1 N hydrochloric acid for 2 hours without current application. Each tablet was then transferred to a dissolution media of 900 ml of standard 50 mM pH 7.2 potassium phosphate buffer with 0.9% NaCl. An electric current was applied to the tablet for 24 hours. Tablets in the buffer stage were clamped at 5 or 2.5 mAmps as indicated. Some tablets were tested using a battery (AAA Alkaline). This clamped the voltage at 1.5 volts. Some tablets were tested in pH 5.5 saline without a buffer. A 1 ml sample was withdrawn at each time.

HPLC Analysis: an Agilent 1100 series HPLC with auto sampler and dual wavelength detector was used. The mobile phase was acetonitrile to water with 0.5% formic acid (60:40 v/v). The flow rate was 1.2 mL/min and the sample injection volume was 50 µL and the wavelength of detection was 214 nm. The column used was a 150 by 4.6 mm Eclipse Plus C18 column (Agilent).

Apparatus II wasn't suitable for running dissolution studies. The paddle tended to hit the zinc wire and ruin the tablet. Apparatus I, the basket, wasn't also suitable due to difficulties of applying the electric current to the tablet while rotating. For more practical application of the electric current to the tablet; a modified dissolution set-up was used (FIG. 26). The tablet location was above the paddle.

Figure 27:
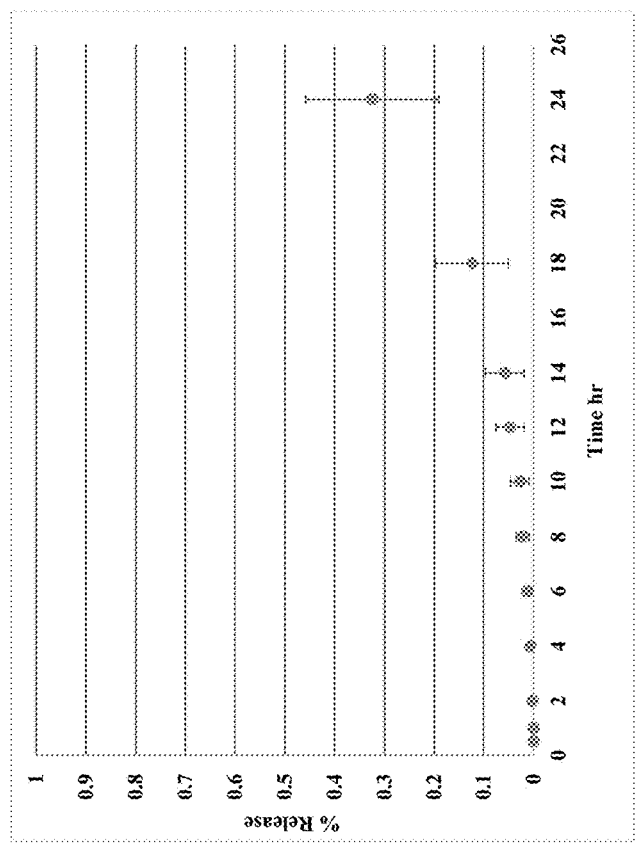
FIG. 27 is a chart depicting the release profile of ibuprofen from fail-safe tablets in pH 7.2 phosphate buffer where 5 and 2.5 mAmps (mAmperes) were applied.
Figure 28:
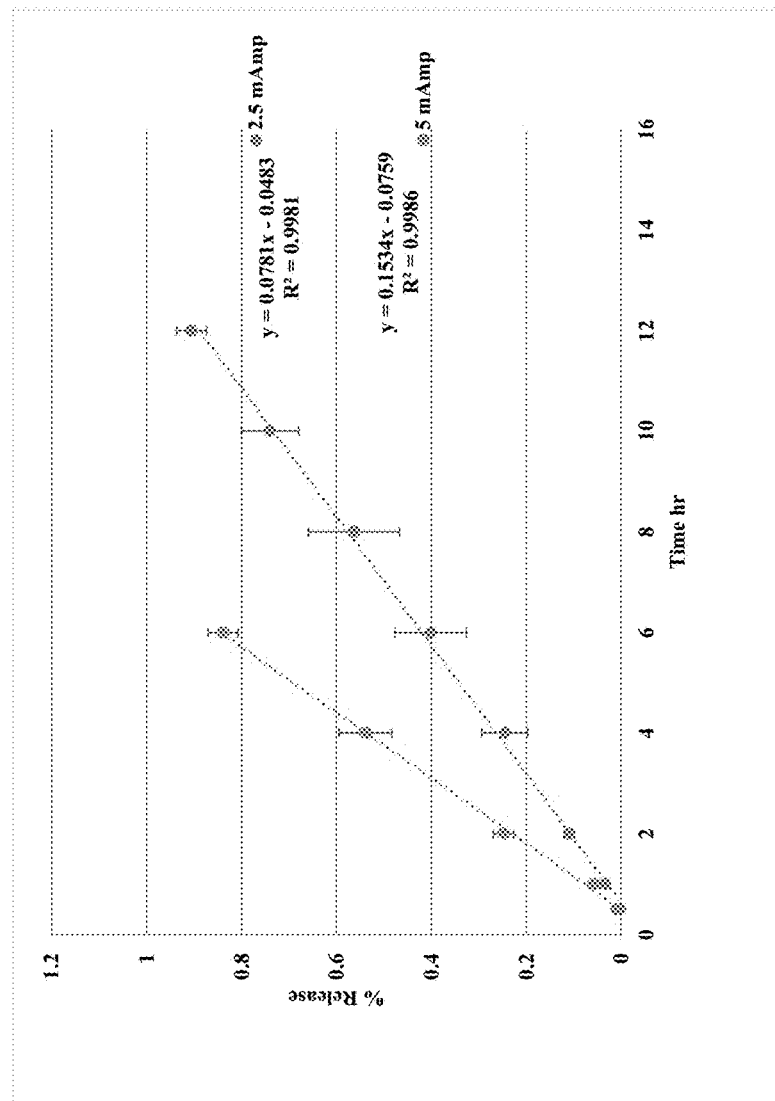
FIG. 28 is a chart depicting the release profile of ibuprofen from fail-safe tablets in pH 7.2 phosphate buffer where 5 and 2.5 mAmps were applied.

FIG. 27 (Release profile of ibuprofen from fail-safe tablets in pH 7.2 phosphate buffer where 5 and 2.5 mAmps (mAmperes) were applied. The zinc cathode was inserted in the tablets. The tablets where pretreated in 0.1 N HCl for two hours). Release profile of ibuprofen from fail-safe tablets in pH 7.2 phosphate buffer where no current was supplied. The tablets where pretreated in 0.1 N HCl for two hours) shows the release profile of ibuprofen in saline (0.9% NaCl) pH 7.2 phosphate buffer when no current was applied. This experiment was done as a control. Less than 15% of the drug was released over 18 hours. This tablet is considered a fail-safe tablet since complete release is triggered upon current application. When 5 mAmp was applied, 80% of the drug was released in 5.9 hours (FIG. 28; Release profile of ibuprofen from fail-safe tablets in pH 7.2 phosphate buffer where 5 and 2.5 mAmps were applied. The zinc cathode was inserted in the tablets. The tablets where pretreated in 0.1 N HCl for two hours). Release profile followed zero order kinetics. In order to investigate the effect of the current on the release of ibuprofen, 2.5 mAmp was also tested. It was found that 80% of the drug was released in 10.89 hours (FIG. 28).

For further investigation of the release mechanisms; electrodes were switched. In this case the anode was connected to the tablet while the cathode was connected to the medium solution. Results showed that less than 1% drug release was detected over 24 hours (FIG. 29; Release profile of ibuprofen from fail-safe tablets in pH 7.2 phosphate buffer when the zinc anode was inserted in the tablets. The tablets where pretreated in 0.1 N HCl for two hours).

Figure 30:
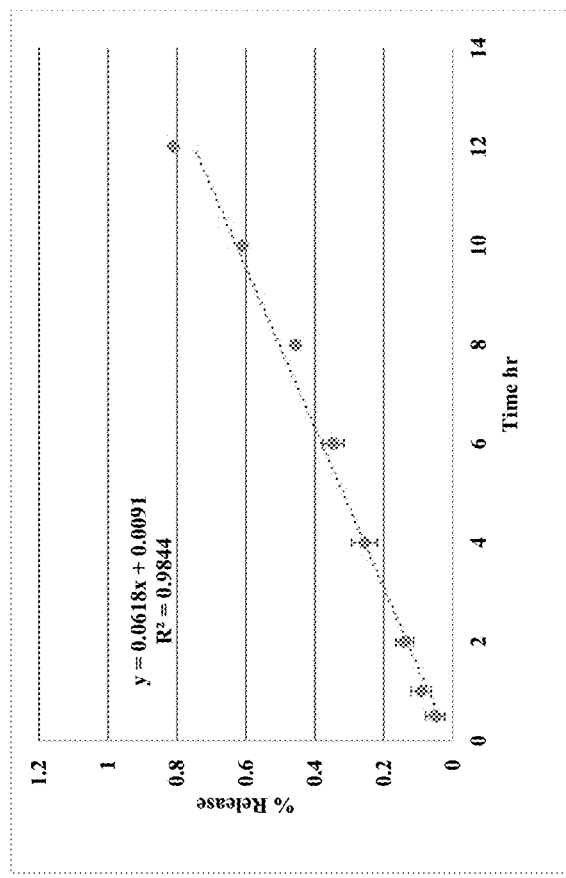
FIG. 30 is a chart depicting the release profile of ibuprofen from fail-safe tablets in pH 7.2 phosphate buffer where 1.5 volts AAA Alkaline battery was used as a power source; the zinc cathode was inserted in the tablets, and the tablets where pretreated in 0.1 N HCl for two hours.

Since the power supply used in the previous experiments only clamps the current, a 1.5 volts AAA battery was used as a power source. This simulates the type of power-supply which would be used in this type of system. The drug release results were similar to the results of the 2.5 mAmps experiment (FIG. 30; Release profile of ibuprofen from fail-safe tablets in pH 7.2 phosphate buffer where 1.5 volts AAA Alkaline battery was used as a power source. The zinc cathode was inserted in the tablets. The tablets where pretreated in 0.1 N HCl for two hours).

The behavior of this tablet was tested in extreme conditions. These conditions were pH 5.5 saline water without any buffer addition to the media. The current applied was 2.5 mAmp. These experiments could determine the validity of using this tablet as a dosage form independent of medium pH, buffer capacity, and microflora concentration. A dosage form that is solely dependent on the electric current application. Results showed that the release rate in pH 5.5 saline was the same as the release rate in pH 7.2 phosphate buffer when 2.5 mAmp current was applied (FIG. 31; Release profile of ibuprofen from fail-safe tablets in pH 5.5 saline water. The zinc cathode was inserted in the tablets. The tablets where pretreated in 0.1 N HCl for two hours).

Kwon I. C., et al prepared a solid matrix made with poly(ethyloxaline) and poly methacrylic acid (PMAA) as an implant. This matrix had the ability to dissolve at pH 5.4 and precipitate at a lower pH. They suspended regular zinc insulin in 10 ml of the mixed polymer solution at pH 5.5. The complex was formed by decreasing the pH of the suspension below pH 5 with 0.1 M HCl solution. It was then compressed into disks and dried for three days. Before the study these disks were pre-swollen in 0.9% saline solution for three days. They found that the amount of insulin released during the 3 days equilibrium period in saline was less than 4% of the initial insulin load. In the release study insulin was released in a stepwise manner. By applying electric current to the matrix, they were able to raise the pH of the matrix and dissolve it. Because water electrolysis produced hydroxyl ions at the cathode, the local pH near the cathode increased. As a result, hydrogen bonding between the two polymers was disrupted causing disintegration of the polymer complex into two water soluble polymers. They did this in a pulsed manner by switching the electric current on and off. The procedure they followed to make the matrix and apply the electric current into it was complicated. Although they developed this matrix as an implant, they found that it was long way from practical application.

Yuk developed a composite of calcium alginate/polyacrylic acid (CPC; Yuk et al., 1992, Pharmaceutical Research, 9(7):955-957). They developed this composite to be used as an electric current-sensitive drug delivery system. They mixed 2 wt. % sodium alginate aqueous solution and 25 wt. % polyacrylic acid aqueous solution with hydrocortisone. To make the gel matrix, they poured calcium chloride solution on the surface of the alginate solution and left it for an hour. The gel matrix was formed from the surface. They immersed the matrix in water for 3 hours to remove unreacted calcium chloride and then cut it into pieces. Finally, they inserted electrodes directly into the polymer matrix and applied electric current to initiate drug release. Although they observed a pulsatile drug release upon application of electric current, their method of preparation suffered several limitations. First, gel preparation process was complicated and time consuming. Second, they inserted the electrodes after cutting the alginate gel into pieces. Finally, the final gel was not dry (was kept wet).

In order to overcome the limitations related to usage of hydrogels and electric capsules for oral sustained drug delivery through current application; the novel basket method was used. The novel basket method allows for making calcium alginate tablets in a controlled manner. Less time is needed for cross-linking. Also, the new method allows for an in situ insertion of the electrode in the tablet at the time of tablet fabrication. Most importantly, this method offers an end product, tablet, without the need for further cutting of the gel. Finally, the tablet is dry. This is important for electronics' maintenance (battery and sensor) outside the tablet on the long term run.

The pH of the solution is a critical parameter controlling the solubility of the alginate (Rehm, 2009, Alginates: Biology and Applications, Springer-Verlag). The mannuronic acid and guluronic acid which alginate comprises, have pKa values of 3.38 and 3.65, respectively. The carboxylic groups of these acids can be protonated by addition of inorganic acids. Therefore, if the pH of the solution is lowered below the pKa of the constituting acids, the soluble sodium salt is converted to insoluble alginic acid. (Rehm, 2009, Alginates: Biology and Applications, Springer-Verlag).

The mechanism by which the electric current releases the drug is not quite understood. At neutral pH the carboxylic acid groups of the alginate monomers become partly transferred into ionized carboxylate group (COO—). Thus, more electrostatic repulsion is established among polymer chains facilitating swelling (Ying et al., 2013, J. Appl. Polym. Sci., 127:3898-3909). More relaxed and swelled polymer chain is more susceptible to erosion process by the buffer. Previously, we demonstrated that when zinc wire is used for both electrodes, pH tends to increase at the cathode due to water electrolysis where hydrogen gas is released. It seems that the rise in pH inside the tablet converted the carboxylic groups of the alginic acid into its ionized state. This allowed for relatively fast relaxation and allowed the matrix to erode fast.

In addition, the cathode might have two effects on the tablet. First; the flux of sodium ions towards the cathode could create a high osmotic pressure gradient between the tablet and the media around it. This might increase the flux of water into the tablet, accelerate swelling, and as a result increased drug release. Second; release of ibuprofen could be driven by the electric current itself due to repulsion by the cathode. The release of the hydrogen gas could be another factor to enhance the release rate by creating a hole in the tablet that allows for more solution to get inside the tablet.

The release rate of the drug from the electrolytic tablet could be controlled via application of electric current. Also, different release profiles could be achieved by applying different electric currents (FIG. 28).

Figure 29:
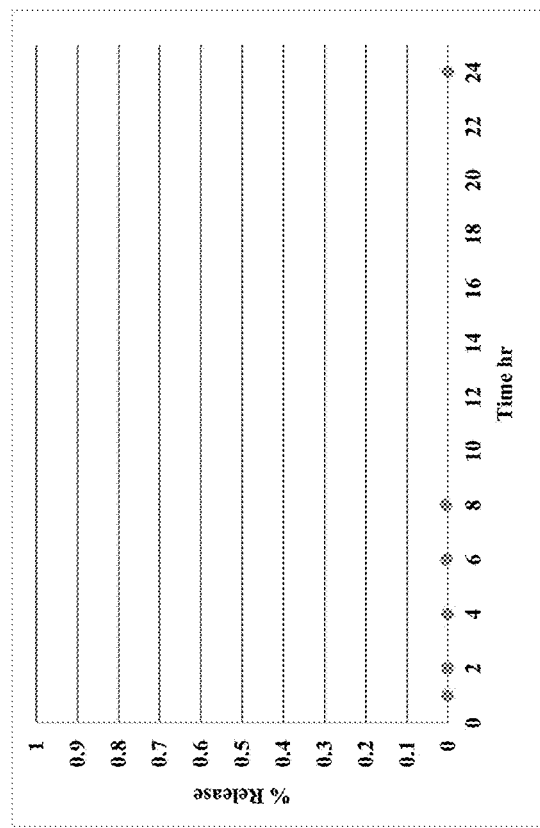
FIG. 29 is a chart depicting the release profile of ibuprofen from fail-safe tablets in pH 7.2 phosphate buffer when the zinc anode was inserted in the tablets.

When the anode was connected to the electrolytic tablet less than 1% drug release was detected over 24 hours. These findings support the hypothesis that mechanisms related to cathode connection to the tablet; increase in pH, hydrogen gas release, osmotic pressure gradient and repulsion by the negative electrode, might be responsible for the release of the drug (FIG. 29).

Figure 31:
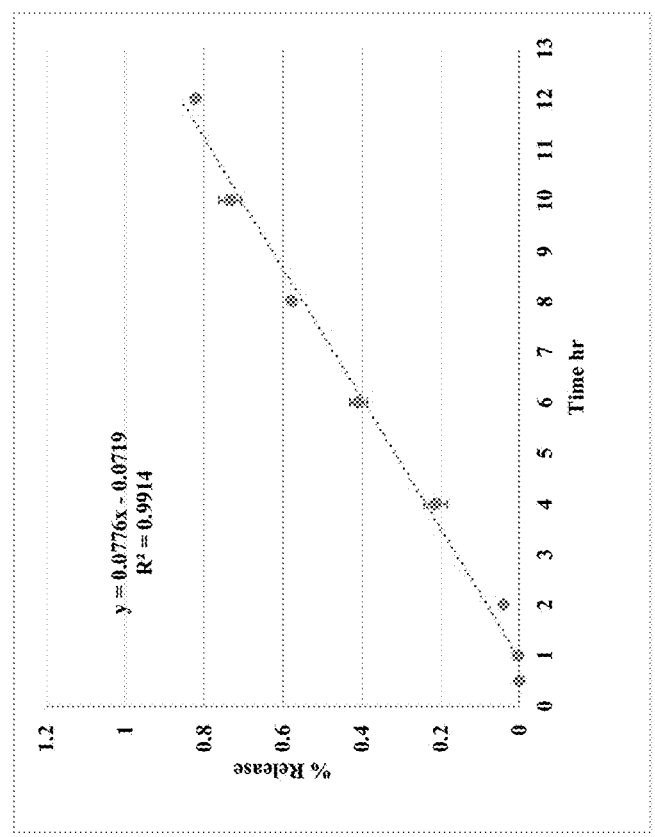
FIG. 31 is a chart depicting the release profile of ibuprofen from fail-safe tablets in pH 5.5 saline water; the zinc cathode was inserted in the tablets, and the tablets where pretreated in 0.1 N HCl for two hours.

FIG. 31 showed that the release rate of the drug in pH 5.5 saline was the same as the release rate in pH 7.2 phosphate buffer when 2.5 mAmp current was applied. These results suggest that the release of this tablet is independent from pH or the buffer capacity of the media. Hence, this electrolytic tablet might be useful for targeted colonic drug delivery. For colonic drug delivery, drug release in the small intestine is avoided. There are several approaches to specifically deliver drugs to the colon. These include prodrugs and synthetic or natural polymer-based delivery systems. These systems are microbially activated by the enzymes secreted by colonic microflora (Sinha and Kumira, 2003, European Journal of Pharmaceutical Sciences, 18:3-18). Since the activity of the microbial enzymes is susceptible to diet, drug intake and environmental factors, the reliability of using these systems is questionable. Moreover, the performance of these systems might vary when introduced to diseased GIT conditions. In abnormal conditions, the GIT normal bacterial flora becomes disturbed (Sinha and Kumira, 2003, European Journal of Pharmaceutical Sciences, 18:3-18). The electrolytic tablet doesn't show this variability. It releases the drug in a uniform manner whether pH is 5.5 or 7—which is the range of pH in the colon (Wilson, M., 2005, Cambridge University Press)—and regardless of buffer capacity. In addition, drug can be released at different rates by adjusting amperage.

An electrolytic calcium alginate tablet was thus developed. The matrix for the tablet was a fail-safe tablet. This tablet releases the drug on demand when the electric current is switched on. Otherwise, less than 20% of the drug is expected to be released over 24 hours when electric current isn't applied. In comparison to other oral electric dosage forms this tablet has several advantages. First, the production process is cheap and easy to control. Second, the matrix used for the tablet is biodegradable and safe. Third, the release of the drug is not dependent on the contents of the dissolution media or its pH. This novel dosage form can be used for targeted drug delivery in the small intestine and the colon.

Example 7: Caffeine Delayed Release Formulation

A caffeine dosage form was developed, having less than 20% release in 8 hours, and more than 80% release in 12 hours. Caffeine tablets were compressed either on Carver press or Minipress IIBD. In some embodiments, alginate based coatings were used to coat alginate tablets compressed on Carver press. Tablet Specifications: dose: 150 mg; lag-time: less than 20% release in 8 hours; drug release: greater than 80% release in 12 hours.

7.1 Carver Press Compressed Tablets

Tablet Cores Formulation: the tablet cores were made from caffeine monohydrate (Spectrum, USA), sodium alginate (Spectrum), Avicel-PH-102 (FMC Biopolymer), and stearic acid (Spectrum); the proportions are given in Table 8.

TABLE 8

Tablet Core

| Ingredient | % | Amt/kg (g) | Amt/Tablet (mg) |
|---|---|---|---|
| Caffeine Monohydrate | 50 | 500 | 150 |
| Sodium Alginate | 33 | 330 | 16.5 |
| Microcrystalline Cellulose | 16.5 | 165 | 16.5 |
| Stearic Acid | 0.5 | 5 g | 1.5 |

(tablet weight 300 mg)

Tablet Compaction: tablet cores were compressed on a single punch Carver Laboratory Press. The tooling used produced a single convex, round tablet. The parameters of these tablets are shown in Table 9.

TABLE 9

Tablet Specifications

| Parameter | Average |
|---|---|
| Weight | 307 mg |
| Thickness | 3.6 mm |
| Diameter | 11.71 mm |
| Hardness | 134 N |

Tablet Coating: the coating procedure requires two coating formulations. The first coating formulation comprises corn oil. The second coating formulation comprises ethocel. To make the corn oil coating, corn oil was mixed with Avicel PH-102. The mixture was mixed with hot water using a homogenizer. Alginate was added gradually and mixed until the gel was uniform. Finally, sodium stearate was added and mixed. To make the ethocel coating, alginate was mixed with water using a homogenizer. Ethocel was added and mixed until the gel was uniform. All coating solutions were degassed using a desiccator vacuum chamber. Tables 10 and 11 shows a summary of the proportions used in each coating.

TABLE 10

Corn Oil Coating Formulation

| Compendial Name | WT % COMPOSITION | QUANTITY/kg (g) |
|---|---|---|
| Corn Oil | 31.8 | 318 |
| Avicel PH-102 | 2.72 | 27.2 |
| Water | 63.6 | 636 |
| Sodium Alginate | 1.8 | 18 |
| Sodium Stearate | 0.09 | 0.9 |

TABLE 11

Ethocel Coating Formulation

| Compendial Name | WT % COMPOSITION | QUANTITY/kg (g) |
|---|---|---|
| Ethocel | 9.34 | 93.4 |
| Water | 86 | 860 |
| Sodium Alginate | 4.67 | 46.7 |

Process: both coating solutions were used to coat the tablets. Before starting the coating process, the tablets were sprayed with 4 M Calcium Chloride solution. The oil coating was sprayed three times intermittently with Calcium Chloride solution until a 56% or 64% weight gain was achieved as indicated. While the tablets are still wet, an Ethocel-Sodium Alginate coat was added after spraying the tablets with Calcium Chloride solution. Oil tends to percolate from the alginate coating upon drying. The Ethocel-coating was applied while the tablets were still wet to prevent oil from leaching from the coating layer. Ethocel coating seals the oil layer on the tablet. The resulting tablets were dried at 40° C. until there was no additional water loss.

Figure 32:
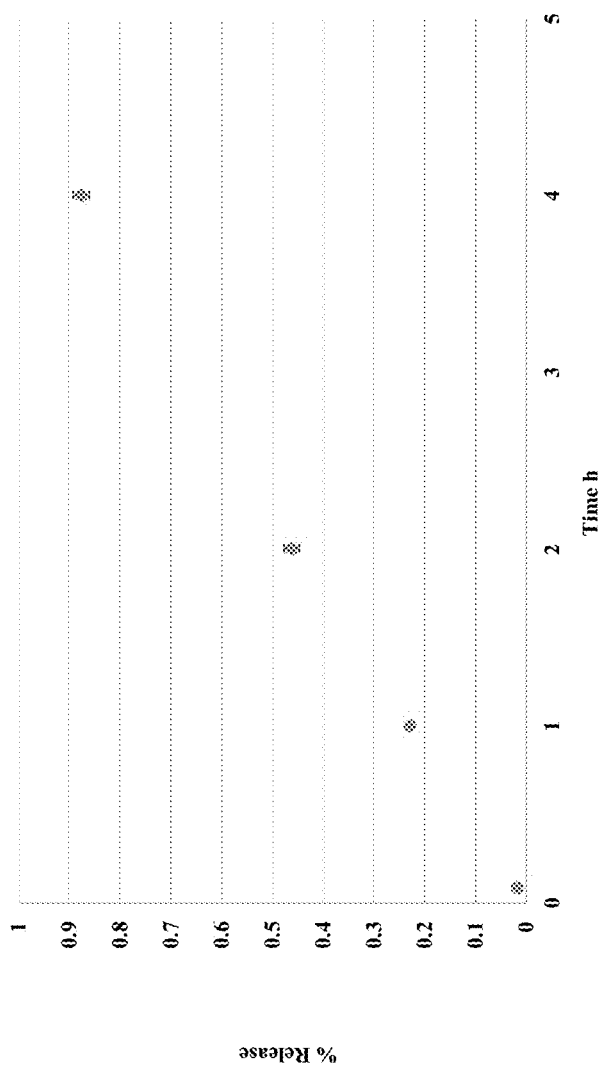
FIG. 32 is a chart depicting the release profiles of tablets compressed on the Carver press; dissolution was tested in pH 7.2 phosphate buffer.

Tablet Core Results: the release profile of uncoated core tablets is shown in FIG. 32, which shows the release profiles of tablets compressed on the Carver press, where dissolution was tested in pH 7.2 phosphate buffer.

Figure 33:
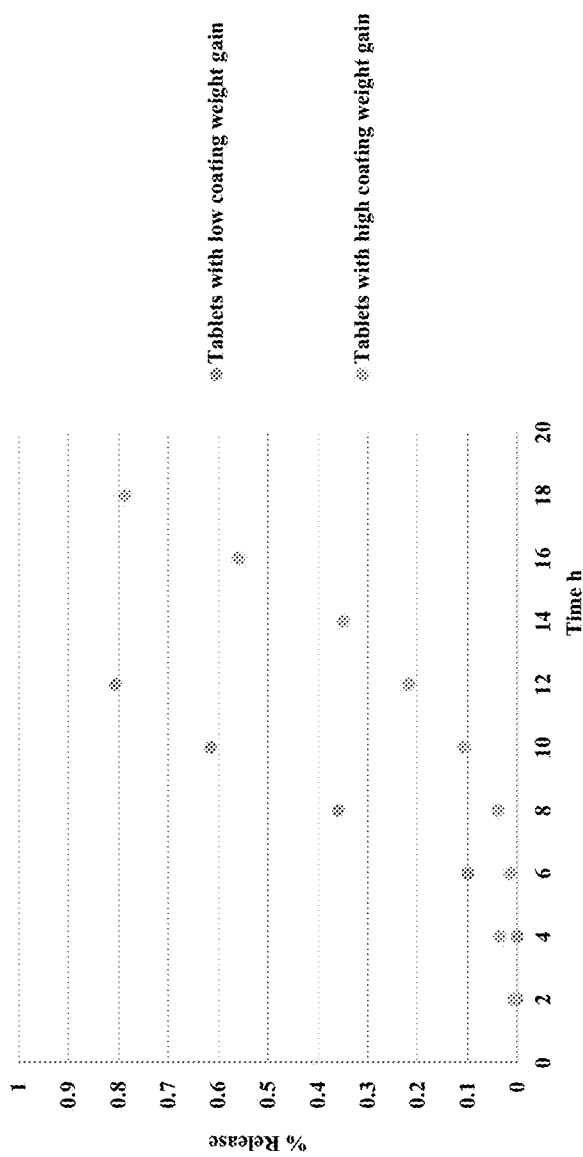
FIG. 33 is a chart depicting the release profile of low coating weight gain tablets (gray), and high coating weight gain tablets (yellow).

Coated Tablet Results: different weight gains were tested to try to achieve the delayed release profile. FIG. 33 shows the release profiles of low coating weight gain tablets and high coating weight gain tablets.

Tablets with low weight gain:
    The weight of the core compressed tablet: 0.3122 g
    The weight gain of oil coating (wet): 56%
    The weight gain of the ethocel coating (wet): 30%
    The weight of the dried tablet: 0.5956 g
    The weight gain of the dried tablet: 47%

Tablets with high weight gain:
    The weight of the core compressed tablet: 0.0.3011 g
    The weight gain of oil coating (wet): 64%
    The weight gain of ethocel coating (wet): 26%
    The weight of the dried tablet: 0.6554 g
    The weight gain of the dried tablet: 54%

A tablet formulation with traditional tablet compaction and traditional film coating can thus be made to retain caffeine for up to 8 hours and release 80% by 12 hours. These formulations utilize a novel sodium alginate formulation. Process parameters for high speed tablet presses may need additional optimization for powder flow. A wet granulation process can achieve better flow. Temperature and air flow parameters for coating in a perforated can prevent oil leakage during the first oil coating and subsequent ethyl cellulose coating. Over drying during these steps can cause leaching of oil during the process. A low temperature process can be performed during the coating step.

7.2 Minipress IIBD Compressed Tablets

Tablet Cores Formulation: the tablet cores were made from Caffeine Anhydrous (Spectrum), Sodium Alginate (Spectrum), Avicel-PH-102 (FMC Biopolymer), Lactose Monohydrate (Spectrum) and Stearic Acid (Spectrum). The proportions are given in Table 12.

TABLE 12

Core Formulation

| Ingredient | % | Amt/kg (g) | Amt/Tablet (mg) |
|---|---|---|---|
| Caffeine Anhydrous | 50 | 500 | 150 |
| Sodium Alginate | 16.5 | 165 | 16.5 |
| Microcrystalline Cellulose | 16.5 | 165 | 16.5 |
| Lactose | 16.5 | 165 | 16.5 |
| Stearic Acid | 0.5 | 5 g | 1.5 |

Tablet Compaction: tablet cores were compressed on a Minipress IIBD with B-tooling at 37 RPM. A generic simvastatin tooling was used. This tooling produced a double convex, round tablet with a diameter of 12.27 mm. The specification for the tablet core was weight of 300 mg and hardness average of 60 N. This produced a core thickness of 3.95 mm. A summary of the tablet specifications are given in Table 13.

TABLE 13

Tablet Specifications

| Parameter | Average |
|---|---|
| Weight | 302.8 mg |
| Thickness | 3.95 mm |
| Diameter | 12.27 mm |
| Hardness | 60 N |

Figure 34:
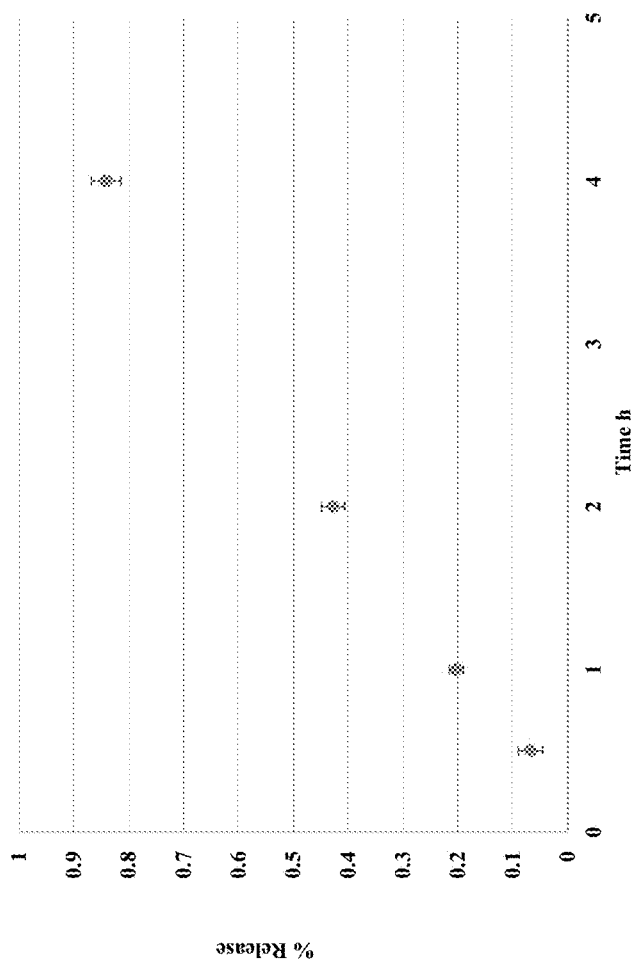
FIG. 34 is a chart depicting the release profile of tablets made with lactose formulation and compressed on a Mini-press; dissolution was tested in pH 7.2 phosphate buffer.

Because it was somewhat more difficult to produce tablets with similar hardness on the Minipress using the formulation used on the Carver press, lactose was added to increase the hardness of the tablets. It was found that more than 80% of the drug can be released in four hours when low hardness (60 N) is applied. FIG. 34 shows the release profiles of tablets made with lactose formulation.

The addition of lactose was necessary to increase the hardness of the tablets compressed on the Minipress IIBD. The release profile of these tablets was very similar to the release profile of tablets compressed on the Carver press (FIG. 33). Hence, these tablets can be used for alginate coating to achieve the required delayed release profile.

Example 8: Caffeine Delayed Release Formulation

A caffeine dosage form which has less than 20% release in 8 hours and more than 80% release in 12 hours was developed, including development of a new coating technique which provides a long lag-time and protection for the tablet in the acid stage.

Materials and Methods

Glycerol (Fisher, USA), stearic acid (N.F, Spectrum, USA), alginic acid sodium salt (Sigma Aldrich, United Kingdom), calcium chloride dihydrate (Fisher, USA), ethyl cellulose (Acros Organics, USA), microcrystalline cellulose, PH 102 (FMC Biopolymer, USA), castor oil (Ruger, USA), caffeine monohydrate (MP Biomedicals, USA), guarana seed extract powder (NutriCargo, USA), titanium dioxide (Fisher, USA), glassware dryer (Precision Scientific, USA), and homogenizer (Polytron, Switzerland).

For dissolution studies: dissolution bath (Vankel VK 7010 dissolution apparatus, Cary, N.C.), temperature control (Vankel 17-2200, Cary, N.C.), and USP standard 40 mesh basket (Fisher). Potassium phosphate monobasic (Sigma Aldrich, USA) and sodium hydroxide (Fisher, USA) were used to prepare the buffer. HPLC grade acetonitrile (Fisher, USA) was used in preparation of mobile phase.

The proportions used to make the gel for the calcium alginate tablets, the coating solutions and the cross-linking solutions are given in Tables 14-18.

TABLE 14

Alginate Gel Composition

| Compendial Name | WT % Composition | Quantity (g) |
|---|---|---|
| Alginic acid sodium salt | 3.43 | 1.6 |
| Stearic acid | 8.58 | 4 |
| Caffeine monohydrate | 25.75 | 12 |
| Guarana extract | 2.15 | 1 |
| Deionized water | 60.0 | 28 |

TABLE 15

Castor Oil Emulsion Coating Composition

| Compendial Name | WT % Composition | Quantity (g) |
|---|---|---|
| Castor oil | 30.89 | 35 |
| Ethyl cellulose | 3.08 | 3.5 |
| Stearic acid | 2.64 | 3 |
| Alginic acid | 1.58 | 1.8 |
| Deionized water | 61.78 | 70 |

TABLE 16

Microcrystalline Cellulose Coating Composition

| Compendial Name | WT % Composition | Quantity (g) |
|---|---|---|
| Alginic acid | 4.58 | 2.5 |
| Microcrystalline cellulose | 9.17 | 5 |
| Titanium dioxide | 1.83 | 1 |
| Deionized water | 84.4 | 46 |

TABLE 17

Tablets Cross-linking Solution Composition

| Compendial Name | WT % Composition | Quantity (g) |
|---|---|---|
| Calcium chloride | 12.81 | 14.7 |
| Deionized water | 87.18 | 100 |

TABLE 18

Coating Cross-linking Solution Composition

| Compendial Name | WT % Composition | Quantity (g) |
|---|---|---|
| Calcium chloride | 34.83 | 58.8 |
| Glycerol | 5.92 | 10 |
| Deionized water | 59.24 | 100 |

The procedure for making the tablets includes the following steps:
1. 12 g of caffeine was mixed with 28 mL water until completely dissolved;
2. 1.6 g alginate was added and mixed;
3. 1 g guarana seed extract powder and 4 g stearic acid were added to the mixture and stirred until a uniform gel was formed;
4. The gel was degassed to release gas bubbles;
5. 0.5 mL of the gel was dispensed in a basket (1 cm diameter), previously wetted in a 1 molar calcium chloride solution;
6. The basket was soaked in the cross-linking solution for 20 seconds;
7. The tablets were removed from the cross-linking solution and dried at room temperature for 5 hours followed by air drying in a glassware dryer at 35° C. for 4 hours.

The tablets were coated with castor oil coating and microcrystalline coating. 35 g of castor oil were mixed with 3.5 g of ethyl cellulose and 3 g of stearic acid. The mixture was heated until ethyl cellulose and stearic acid were melted. The hot mixture was emulsified with 70 mL of hot water using a homogenizer. 1.8 g of alginate was added gradually and mixed until a uniform gel was formed. The microcrystalline cellulose (MCC) coating was made by mixing 5 g of MCC, 2.5 g alginate, 1 g titanium dioxide in 46 mL water. The cross-linking solution was made with 4 molar calcium chloride solution and glycerol (90:10 v/v).

The following procedure was used for coating the delayed release calcium alginate tablets:
1. Before coating, tablets were dipped in calcium chloride solution for 5 seconds and the extra solution was removed;
2. Tablets were dipped in the castor oil coating solution for 1 minute; thereafter, they were washed in deionized water to remove excess coating material;
3. Tablets were dipped in calcium chloride solution for 25 seconds and the extra solution was removed;
4. Steps 2 and 3 were repeated two more times with 20 and 15 seconds crosslinking time in calcium chloride solution;
5. Tablets were dipped in the MCC coating for 1 minute, and extra coating was washed away with deionized water;
6. The coated tablets were air dried in a glassware dryer at 35° C. for 6 hours.

For the enteric coated tablets, the following procedure was used:
1. Before coating, tablets were dipped in calcium chloride solution for 5 seconds and the extra solution was removed;
2. Tablets were dipped in the castor oil coating solution for 1 minute; thereafter, they were washed in deionized water to remove excess coating material;
3. Tablets were dipped in calcium chloride solution for 20 seconds and the extra solution was removed;
4. Tablets were dipped in the MCC coating for 1 minute and extra coating was washed away with deionized water;
5. Tablets were dipped in calcium chloride solution for 20 seconds and the extra solution was removed;
6. The coated tablets were air dried in a glassware dryer at 35° C. for 6 hours. The coated tablets were treated in 0.1 N HCl for two hours prior to the buffer stage. Release profile of tablets were tested in pH 7.2 phosphate buffer media for 24 hours. The release was performed in 900 ml media. USP Apparatus I was used at 37° C. and a speed of 50 RPM.

Results and Discussion

Figure 35:
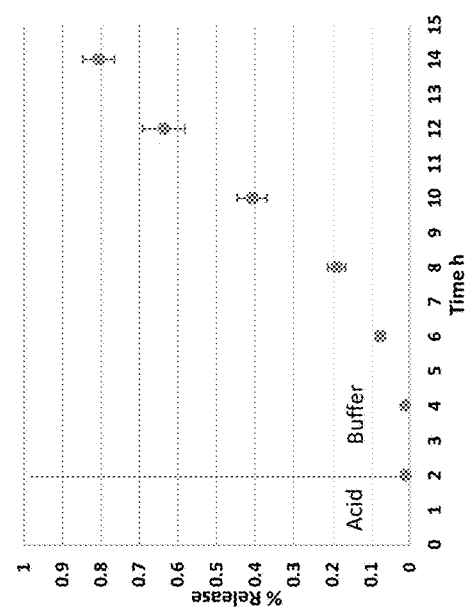
FIG. 35 is a chart depicting the release profile of tablets coated with three castor oil coats and 1 MCC coat; the coated tablet released less than 20% of the drug in 8 hours and 80% in 14 hours.
Figure 36:
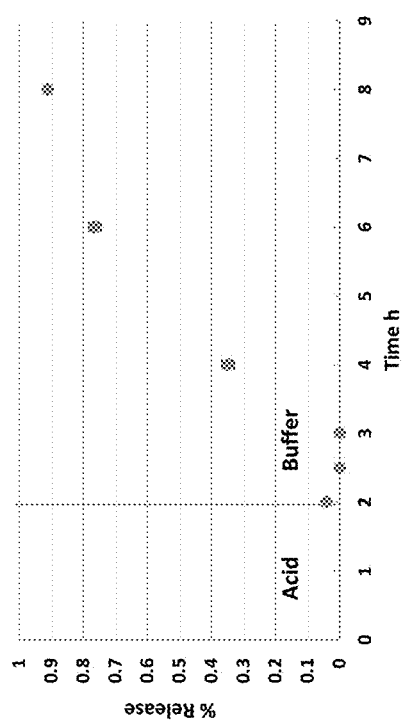
FIG. 36 is a chart depicting the release profile of the enteric coated tablets, coated with 1 castor oil coat and 1 MCC coat.

The current gel congealed tablet core does little to produce a significant lag-time. A coating would need to be used to delay the core's exposure to water. This would provide a desired lag-time. A Seal coating was made using an oil dispersion of castor oil or corn oil dispersed sodium alginate. Calcium Chloride solution was used to bind the layers of these oil dispersions together. The appropriate number of oil dispersion layers was determined to be three. FIG. 35 shows the release profile of the tablets coated with three castor oil coats and 1 MCC coat. The coated tablet released less than 20% of the drug in 8 hours and 80% in 14 hours. FIG. 36 shows the release profile of the enteric coated tablets, coated with 1 castor oil coat and 1 MCC coat. When dissolution profiles using three coatings (FIG. 35) is compared to a single coat (FIG. 36), it is observed that the three coatings are necessary for providing an 8-hour lag-time. A last coat using MCC was used to prevent the oil form the oil coats from leaching out of the tablets.

Conclusion

The tablets coated with three castor oil coats and one MCC coat provided less than 20% release in 8 hours and 80% release in 14 hours. Delayed release coating can be achieved with one coat of castor oil and one coat of MCC.

Example 9: Tamper Resistant Tablet

The invention uses an alginate formulation to fabricate a tamper resistant tablet. Use of an alginate formulation of the invention results in a cross-linked alginate matrix which is hard and not crushable. The alginate matrix neither erodes nor breaks when friction or excessive force is applied. A tablet made with the resulting alginate matrix does not break without scoring the tablet, and the tablet does not break while tested using a tablet hardness tester. In order to break the tablet in half, the tablet must be cut with a razor or a knife.

The resulting alginate matrix made with the alginate formulation of the invention does not erode or break down when exposed to alcohol, acid or water. Erosion of the alginate matrix is only possible when the tablet is placed in a neutral or basic media which has a calcium chelator included. Neither of these are common solvents.

Sustained release products must be tested in alcohol to make sure that the drug does not burst from the dosage form. The polymer in this matrix would shrink and decrease its release rate in the presence of alcohol.

As a result, the alginate matrix used for making a tablet of the invention is extremely tamper resistant, because the tablet cannot be crushed or dissolved to extract the drug. This provides an advantage for tablets containing controlled substances, because the drug or active ingredient cannot be removed from the tablet for later IV (intravenous) injection.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:
1. A method of making a tamper-resistant tablet, comprising:

dipping a mesh basket in a cross linking solution,
filling the basket with a formulation comprising an alginate, and
dipping the basket containing the formulation in a cross linking solution to afford a tablet.

2. The method of claim 1, wherein the formulation further comprises at least one selected from the group consisting of a fatty acid, a stearate, ethyl cellulose, and a drug.

3. The method of claim 1, further comprising covering the mesh basket in filter paper.

4. The method of claim 1, further comprising drying the tablet in an oven.

5. The method of claim 1, further comprising the steps of:
dipping the basket containing the formulation in a at least one additional coating solution;
dipping the basket containing the formulation in a cross-linking solution; and
air-drying the tablet.

6. The method of claim 5, wherein the at least one additional coating solution comprises an oil and a cellulose, and wherein the weight ratio of oil to cellulose in the at least one additional coating solution is about 10:1.

7. A tamper resistant tablet produced using the method of claim 6.

8. The method of claim 1, wherein the crosslinking solution comprises calcium chloride.

9. The method of claim 1, wherein the step of filling the basket with a formulation comprising an alginate further comprises the step of inserting an electrode into the formulation.

10. The method of claim 1, wherein the step of dipping a mesh basket in a cross linking solution is preceded by the step of selecting a basket size and shape.

11. A drug dosage form comprising a core, a first coating disposed over the core, and a second coating disposed over the first coating;
wherein the core comprises an alginate, a drug, and a fatty acid;
wherein the first coating comprises calcium alginate, cellulose, and an oil;
wherein the second coating comprises calcium alginate and cellulose; and
wherein the weight ratio of oil to cellulose in the first coating is about 10:1.

12. The drug dosage form of claim 11, wherein the drug is released from the formulation following a uniform zero-order release rate.

13. The drug dosage form of claim 11, wherein less than about 20% of the drug is released in about 8 hours.

14. The drug dosage form of claim 11, wherein the fatty acid is stearic acid.

15. The drug dosage form of claim 11, wherein an electrode is attached to the drug dosage form.

16. The drug dosage form of claim 11, wherein the drug is selected from the group consisting of: a weak acid, a weak base, a zwitterion, and a neutral compound.

17. A method of delivering a drug to a subject, the method comprising administering to the subject the drug dosage form of claim 11.

18. The method of claim 17, wherein the delivery is selected from the group consisting of oral delivery and subcutaneous delivery.

19. The method of claim 17, wherein less than about 20% of the drug is released from the formulation in about 8 hours.

20. The method of claim 17, wherein more than 80% of the drug is released from the formulation in about 12 hours.

21. The drug dosage form of claim 11, wherein the alginate in the core is selected from the group consisting of an alginate gel and an alginate powder.

22. The drug dosage form of claim 11, wherein the cellulose in the first coating or the cellulose in the second coating is selected from the group consisting of microcrystalline cellulose and ethylcellulose.

23. The drug dosage form of claim 11, wherein the core further comprises microcrystalline cellulose and wherein the weight ratio of microcrystalline cellulose to alginate is 3:1.

* * * * *